US012636030B2

(12) United States Patent
Hibner et al.

(10) Patent No.:    US 12,636,030 B2
(45) Date of Patent:        May 26, 2026

(54) CIRCULARITY SYSTEMS AND METHODS FOR HIGH ARTICULATION SURGICAL TOOLS

(71) Applicant: Cilag GmbH International, Zug (CH)

(72) Inventors: John A. Hibner, Mason, OH (US); Mark A. Davison, Maineville, OH (US); Konstantin Zabotkin, Mason, OH (US); Thomas B. Remm, Cincinnati, OH (US); Veaceslav Arabagi, Cambridge, MA (US); Lesley Wang, Braintree, MA (US); Grace Elizabeth Olsen, Cambridge, MA (US); Robert Andrew Desanti, Somerville, MA (US)

(73) Assignee: Cilag GmbH International, Zug (CH)

( * ) Notice: Subject to any disclaimer, the term of this patent is extended or adjusted under 35 U.S.C. 154(b) by 299 days.

(21) Appl. No.: 18/345,286

(22) Filed: Jun. 30, 2023

(65) Prior Publication Data

US 2025/0000534 A1    Jan. 2, 2025

(51) Int. Cl.
| | |
|---|---|
| *A61B 34/30* | (2016.01) |
| *A61B 17/29* | (2006.01) |
| *A61B 34/00* | (2016.01) |
| *A61B 17/00* | (2006.01) |

(52) U.S. Cl.
CPC .............. *A61B 17/29* (2013.01); *A61B 34/71* (2016.02); *A61B 2017/0023* (2013.01); *A61B 2017/00473* (2013.01); *A61B 2017/2902*
(2013.01); *A61B 2017/2927* (2013.01); *A61B 2034/301* (2016.02); *A61B 2034/305* (2016.02)

(58) Field of Classification Search
CPC ......... A61B 34/00; A61B 34/30; A61B 34/71; A61B 17/29; A61B 2017/0023; A61B 2017/00473; A61B 2017/2902
See application file for complete search history.

(56) References Cited

U.S. PATENT DOCUMENTS

| | | | | |
|---|---|---|---|---|
| 2007/0123855 A1* | 5/2007 | Morley | .................. | A61B 34/71 |
| | | | | 606/50 |
| 2018/0132887 A1* | 5/2018 | Asher | ................ | A61B 17/2804 |
| 2020/0129198 A1* | 4/2020 | Davison | ................. | A61B 34/71 |

* cited by examiner

*Primary Examiner* — Vi X Nguyen
(74) *Attorney, Agent, or Firm* — Vorys, Sater, Seymour and Pease LLP

(57) ABSTRACT
A method of replacing a consumable of a surgical tool includes securing the surgical tool, which includes a drive housing, an elongate shaft, an end effector arranged at a distal end of the shaft and including opposing first and second jaws, a wrist interposing the shaft and the end effector, and a plurality of drive cables extending proximally from the end effector and through the wrist. The method further includes moving the shaft proximally away from the end effector and deeper into the drive housing, detaching the drive cables from the jaws, removing the end effector and the wrist from proximal portions of the surgical tool, replacing the consumable of the surgical tool, reconnecting the end effector and the wrist to the proximal portions of the surgical tool, reconnecting the drive cables to the jaws, and moving the elongate shaft distally toward the wrist and the end effector.

20 Claims, 12 Drawing Sheets

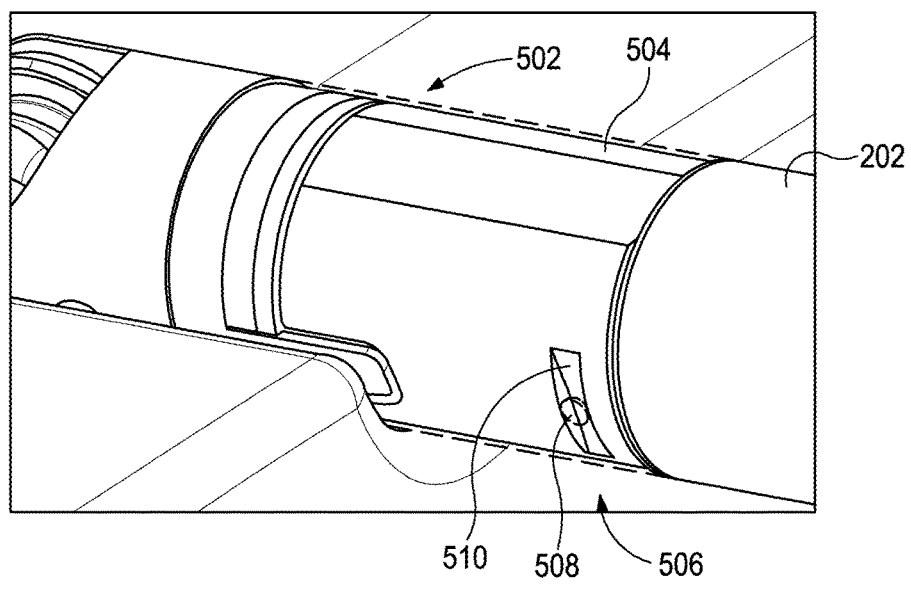
FIG. 5C
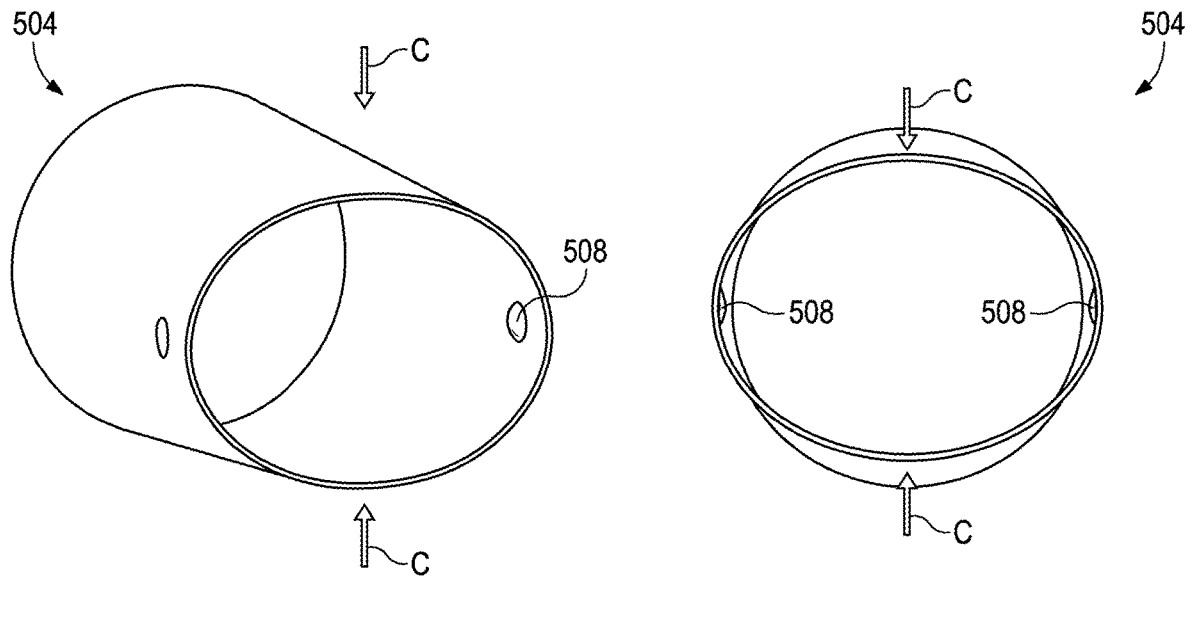
FIG. 5D                    FIG. 5E

CIRCULARITY SYSTEMS AND METHODS FOR HIGH ARTICULATION SURGICAL TOOLS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

MIS instruments incorporate various high-wear components that, over time, can mechanically or physically degrade and thereby limit the useful life of the instrument. Consequently, most MIS instruments are designed to be used only for a predetermined number a procedures, following which the instrument is often discarded. As can be appreciated, this can have an adverse impact on the environment.

In an effort to maintain the value of products, while simultaneously not creating additional environmental waste, companies and manufacturers are progressively looking for ways to incorporate "circularity" into their business model. Circularity is an economic model that follows the three "Rs": reuse, reprocess, and recycle, and aims to retain the lifespan of products through repair and maintenance, reusing, remanufacturing, or upcycling.

What is needed is a process or methodology of circularity concerning the reuse and recycling of MIS instruments, which minimizes the impact on the environment.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 5C is an enlarged isometric view of the interconnection between the proximal clevis sleeve and the distal end of the shaft, according to one or more embodiments.

FIGS. 5D and 5E are isometric and end views, respectively, of the proximal clevis sleeve of FIG. 5C, according to one or more embodiments.

DETAILED DESCRIPTION

The present disclosure is related to surgical tools and, more particularly, to prolonging the lifespan of surgical tools by implementing circularity systems and methods that result in replacement of one or more consumables included in the surgical tool.

The utilization or "lifespan" of a majority of robotic (and non-robotic) surgical tools is often limited due to the life or durability of just a few components within the surgical tool, referred to herein as "consumables". Embodiments disclosed herein describe how the design of the surgical tool can be modified to enable the consumable to be replaced rather easily, without requiring the surgical tool to be completely disassembled. Accordingly, the embodiments disclosed herein may prove advantageous in mitigating or entirely eliminating the need to scrap an entire surgical tool, but instead rehabilitate the used surgical tool by replacing one or more consumables.

Figure 1:
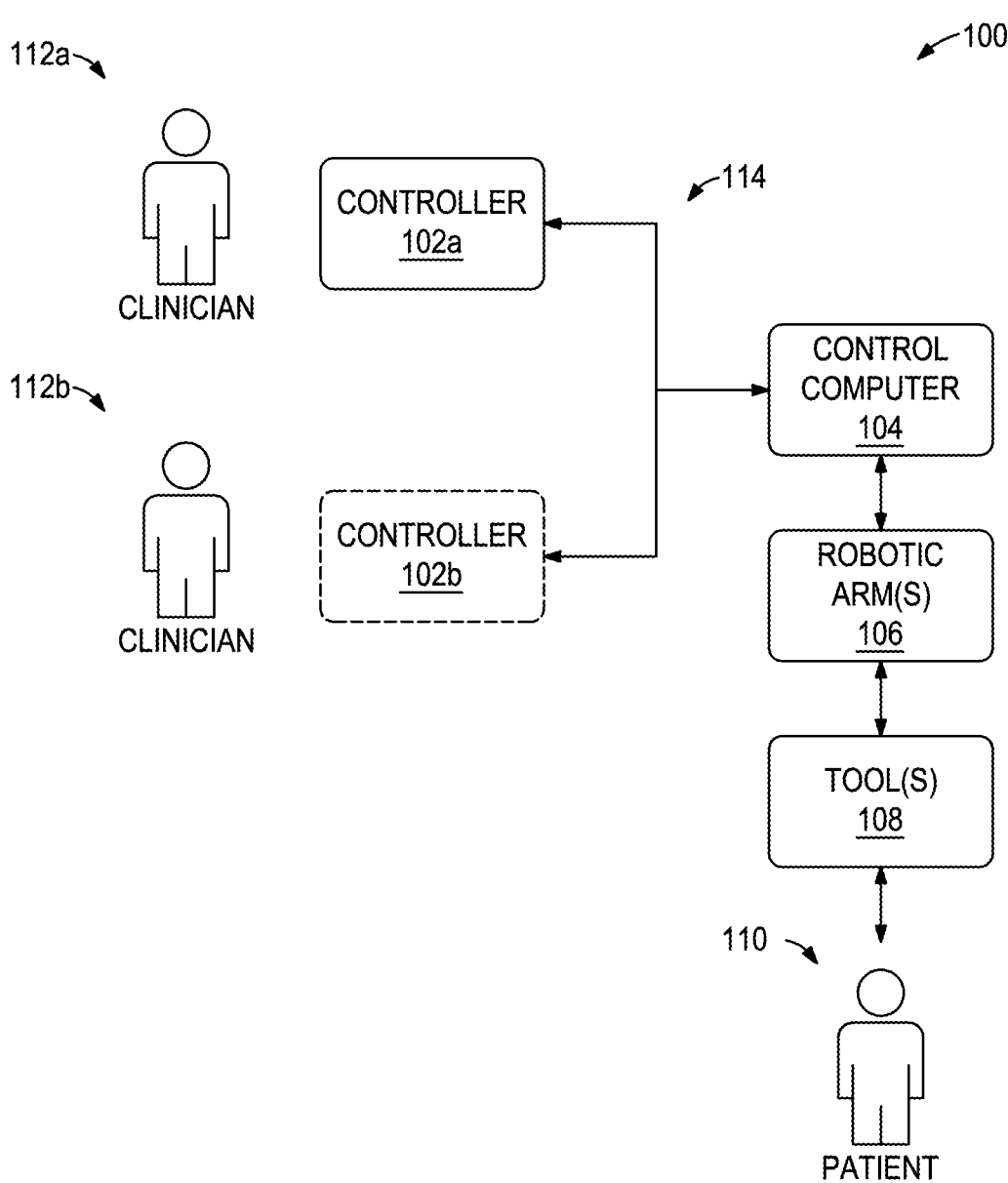
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
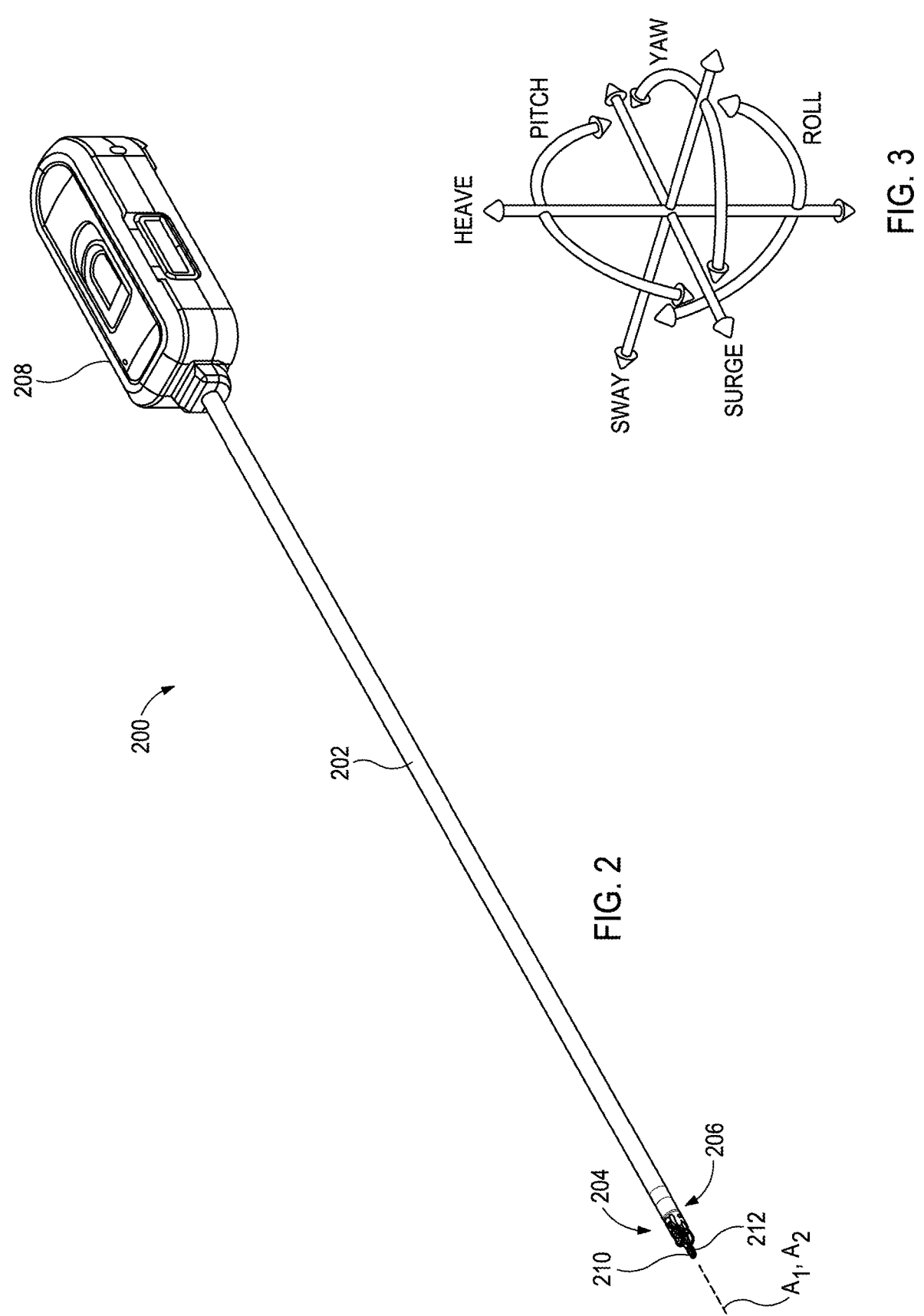
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises a needle driver that includes opposing first (upper) and second (lower) jaws 210, 212 configured to move (articulate) between open and closed positions. As will be appreciated, however, the opposing jaws 210, 212 may alternatively form part of other types of end effectors such as, but not limited to, a surgical scissors, a clip applier, a tissue grasper, a vessel sealer, a combination tissue grasper and vessel sealer, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

Similar to most surgical tools, the surgical tool 200 includes various high-wear components referred to herein as "consumables" that, over time, can mechanically or physically degrade and thereby limit the useful life of the surgical tool 200. Consequently, the surgical tool 200 may be designed to be used for only a predetermined number of procedures. Once the predetermined number of procedures is reached, the operator (e.g., a nurse, a doctor, etc.) may be unable to continue using the surgical tool 200. In such cases, the surgical tool 200 would conventionally be discarded, which can have an adverse impact on the environment.

According to embodiments of the present disclosure, instead of discarding the surgical tool 200, the surgical tool 200 may be subject to circularity processing or a circular economy model or approach designed to reprocess and recycle the surgical tool 200 for further use. In circularity processing, the surgical tool 200 is decommissioned upon reaching the predetermined number of procedures, and then subsequently sent to a service center where trained technicians clean and mount the surgical tool 200 to a disassembly fixture. While mounted to the disassembly fixture, various portions of the surgical tool 200 may be disassembled to access and remove one or more consumables forming part of the surgical tool 200. The removed consumables can then be cleaned and refurbished or replaced with new consumables. The surgical tool 200 may then be reassembled, cleaned, tested, delivered to a distribution center, and subsequently sent to an end user (e.g., a hospital, a surgeon, an operator, etc.) for further use.

Figure 4:
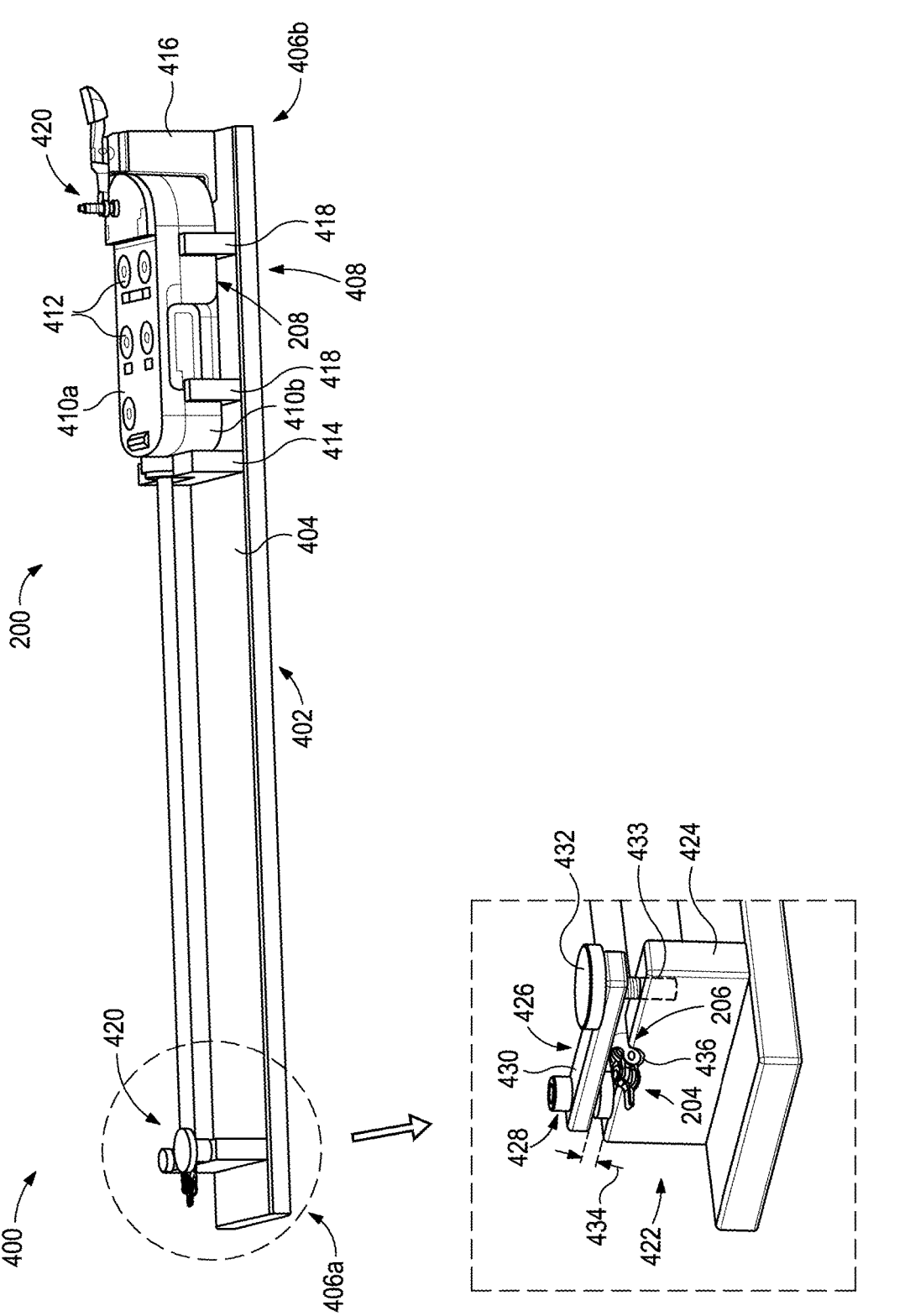
FIG. 4 is an isometric side view of an example circularity processing system, according to one or more embodiments.

FIG. 4 is an isometric side view of an example surgical tool circularity processing system 400, according to one or more embodiments. As illustrated, the surgical tool circularity processing system 400 includes a disassembly fixture 402 configured to receive and mount the surgical tool 200. The disassembly fixture 402 may be provided at a service center that employs technicians trained to clean, disassemble, and refurbish the surgical tool 200, as described herein.

As illustrated, the disassembly fixture 402 provides an elongate base 404 having a first or "distal" end 406a and a second or "proximal" end 406b opposite the distal end 406a. In some embodiments, as illustrated, the base 404 may exhibit a generally rectangular shape, but could alternatively exhibit other shapes without departing from the scope of the disclosure.

A drive housing mount 408 may be provided at the proximal end 406b and configured to receive and seat the drive housing 208, which may include a bottom portion 410a mateable with a top portion 410b. In the illustrated embodiment, the drive housing 208 is shown received within the drive housing mount 408 such that the bottom portion 410a faces upwards and is otherwise exposed. In such embodiments, some or all of the bottom portion 410a may be removed by the technician to access various internal components of the drive housing 208, as described in more detail below. In other embodiments, or in addition thereto, a robotic manipulator (not shown) may be attached to the bottom portion 410a to manipulate and operate one or more drive inputs 412 rotatably mounted to the bottom of the drive housing 208. In other embodiments, however, the drive housing 208 may be received within the drive housing mount 408 with the top portion 410b facing upwards, without departing from the scope of the disclosure.

As illustrated, the drive housing mount 408 may include a plurality of structural elements extending from or otherwise forming part of the body 404 and designed to receive and seat the drive housing 208. More particularly, the drive housing mount 408 may include a cradle or "yoke" 414, a rear support 416, and one or more side supports 418 (two visible) provided at various locations between the yoke 414 and the rear support 416. The yoke 414 may be configured to support the distal end of the drive housing 208, and the rear support 416 may be configured to support the proximal end of the drive housing 208. The side supports 418 may be configured to support the lateral sides of the drive housing 208.

In some embodiments, the drive housing mount 408 may further include a clamp 420 operable to secure the drive housing 208 to the base 404 when properly received within the drive housing mount 408. In some embodiments, as illustrated, the clamp 420 may be mounted to the rear support 416, but could alternatively be mounted other portions of the drive housing mount 408 or the base 404, without departing from the scope of the disclosure.

A vise, referred to herein as an "end effector mount" 422, may be provided and otherwise defined at or near the distal end 406a of the base 404 and configured to receive and seat the distal end of the surgical tool 200. More specifically, and as shown in the enlarged, inset graphic, the end effector mount 422 may include a bracket or stand 424 and a securing clasp or mechanism 426 may be pivotably attached to the stand 424. The securing mechanism 426 may include a pivot joint 428, a securing bar 430 extending from the pivot joint 428, and a mechanical fastener 432 arranged at the end of the securing bar 430 opposite the pivot joint 428. As mounted to the pivot joint 428, the securing bar 430 may be vertically offset a short distance from the stand 424, such that a gap 434 is provided between the securing bar 430 and the top of the stand 424. The gap 434 may be large enough to receive the distal end of the surgical tool 200 when the securing mechanism 426 is secured to the stand 424.

To secure the distal end of the surgical tool 200 to the disassembly fixture 402 and, more particularly, to the end effector mount 422, the distal end of the surgical tool 200 is first placed atop the stand 424 such that the shaft 202 or portions of the wrist 206 engage the top of the stand 424. In some embodiments, as illustrated, the top of the stand 424 may define and otherwise provide an arcuate groove 436 sized to receive and seat the distal end of the surgical tool 200; e.g., the wrist 206 and/or the end effector 204. The securing bar 430 may then be pivoted about the pivot joint 428 until the mechanical fastener 432 is able to locate and mate with a corresponding securing receptor 433 (e.g., a threaded aperture). Operating or otherwise securing the mechanical fastener 432 to the securing receptor 433 may place a load on the distal end of the surgical tool 200, which helps prevent the surgical tool 200 from moving up or down, or translating axially. In the illustrated embodiment, the mechanical fastener 432 comprises a thumbscrew, but could alternatively comprise other types of mechanical fasteners or fastening means suitable for securing the securing bar 430 to the stand 424 and thereby helping to secure the surgical tool 200 to the disassembly fixture 402.

Those skilled in the art will readily appreciate that the end effector mount 422 including the securing mechanism 426 is merely one example embodiment consistent with the principles of the present disclosure. Indeed, other means and configurations of the end effector mount 422 and/or the securing mechanism 426 are possible and contemplated herein, without departing from the scope of the disclosure.

Figure 5A:
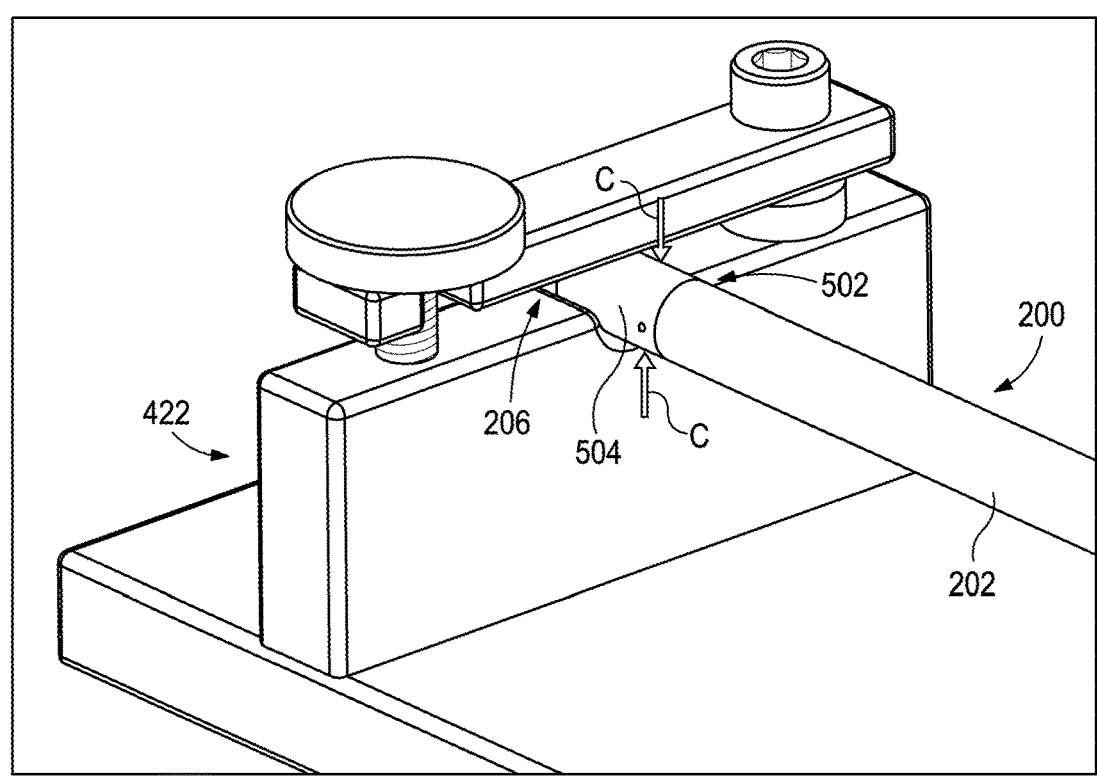
FIGS. 5A and 5B are enlarged isometric views of the distal end of the surgical tool of FIG. 2 as mounted to the end effector mount of FIG. 4.
Figure 5B:
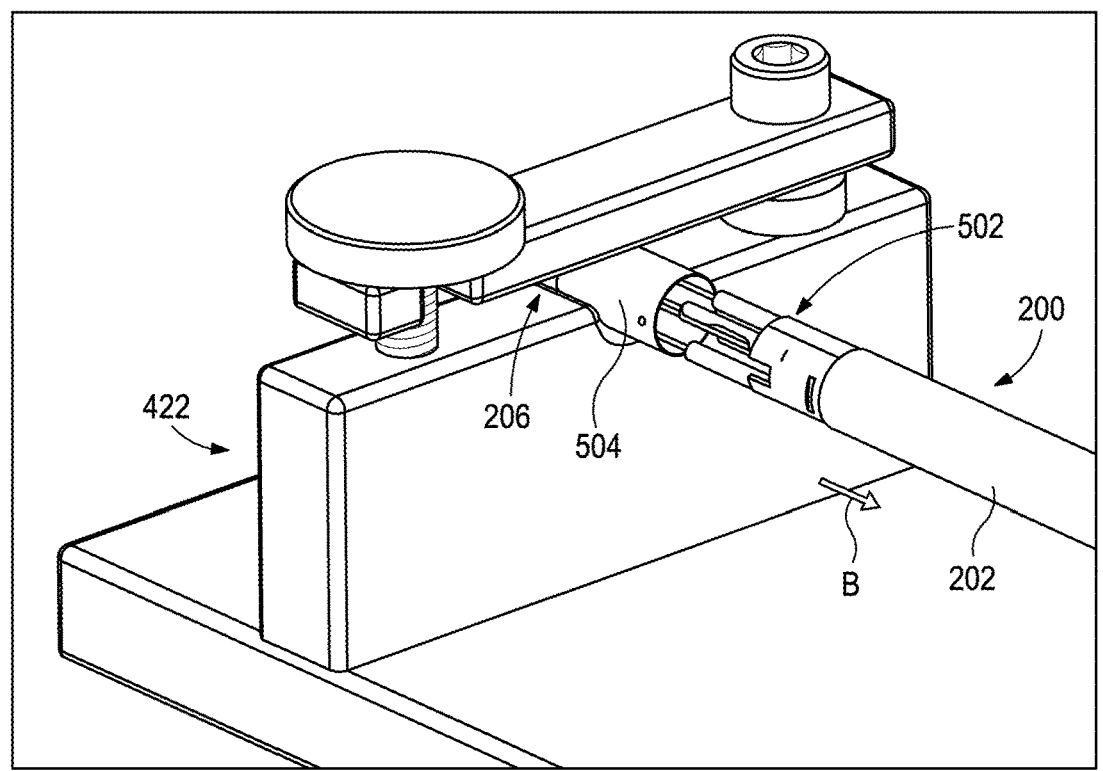

FIGS. 5A and 5B are enlarged isometric views of the distal end of the surgical tool 200 mounted to the end effector mount 422, according to one or more embodiments. Once the distal end of the surgical tool 200 is properly mounted to the end effector mount 422, as shown in FIG. 5A, the shaft 202 may be moved and otherwise translated proximally relative to and away from the end effector 204 (not visible), as indicated by the arrow B in FIG. 5B.

In some embodiments, to move the shaft 202 in the proximal direction B, a distal end 502 of the shaft 202 may need to be released from a proximal clevis sleeve 504 operatively coupled to or forming part of the wrist 206 (mostly occluded). The proximal clevis sleeve 504, alternately referred to as a "shaft adapter," may be a generally cylindrical and hollow structure sized to receive and secure the distal end 502 of the shaft 202 within its interior. The distal end 502 of the shaft 202 may be releasably coupled to the proximal clevis sleeve 504 and releasable from the proximal clevis sleeve 504 by applying opposing, radially-inward directed loads (e.g., pinching) against the proximal clevis sleeve 504, as shown by the arrows C in FIG. 5A. Applying the opposing radial loads C causes the proximal clevis sleeve 504 to elastically deform, which releases the distal end 502 from the proximal clevis sleeve 504 and allows the shaft 202 to move proximally B and away from the proximal clevis sleeve 504.

FIG. 5C is an enlarged, isometric view of the proximal clevis sleeve 504 and the distal end 502 of the shaft 202, according to one or more embodiments. The proximal clevis sleeve 504 is shown in FIG. 5C in phantom (dashed lines)

to enable viewing of an example releasable connection 506 operable to releasably connect the distal end 502 of the shaft 202 to the proximal clevis sleeve 504. In some embodiments, as illustrated, the releasable connection 506 may include one or more dimples or "projections" 508 provided on the inner radial surface of the proximal clevis sleeve 504 and configured to be received within a corresponding one or more grooves 510 defined on the outer radial surface of the shaft 202 at or near the distal end 502.

While the projections 508 are shown provided on the inner radial surface of the proximal clevis sleeve 504 and the grooves 510 are shown on the outer radial surface of the shaft 202, it will be appreciated that the location of the projections 508 and the grooves 510 may be switched, without departing from the scope of the disclosure. Moreover, while FIG. 5C depicts a single projection 508 received within a corresponding single groove 510, the releasable connection 506 may include additional projections 508 and corresponding grooves 510 at other angular locations. In at least one embodiment, for example, a second projection 508 and corresponding second groove 510 may be provided on the angular opposite side of the proximal clevis sleeve 504 (180° offset).

Referring now to FIGS. 5D and 5E, with continued reference to FIG. 5C, illustrated are isometric and end views, respectively, of the proximal clevis sleeve 504, according to one or more embodiments. As illustrated, the proximal clevis sleeve 504 may include two projections 508 arranged on angular opposite sides of the inner radial surface of the proximal clevis sleeve 504. The projections 508 protrude radially inward to be able to be received within corresponding grooves 510 provided on the shaft 202. In some embodiments, as illustrated, the projections 508 may provide rounded and otherwise curved outer surfaces, which may be advantageous in allowing the projections 508 to be more easily received within and dislodged from the grooves 510 as the axial position of the shaft 202 is manipulated.

In some embodiments, the proximal clevis sleeve 504 may be made of an elastic or semi-rigid material, such as a plastic or a metal, which may be able to flex upon assuming the opposing radial loads C, as described above. As illustrated, the opposing radial loads C may be applied to the proximal clevis sleeve 504 at a location perpendicular to the angular position of the projections 508 (90° offset) and otherwise in a plane perpendicular to a plan passing through the projections 508. Upon assuming the opposing radial loads C, the proximal clevis sleeve 504 may flex radially outward at the location of the projections 508 and transition into a generally oval shape. As will be appreciated, this allows the projections 508 to radially separate and dislodge from the corresponding grooves 510, thereby allowing the shaft 202 to be removed from the interior of the proximal clevis sleeve 504.

Figure 6A:
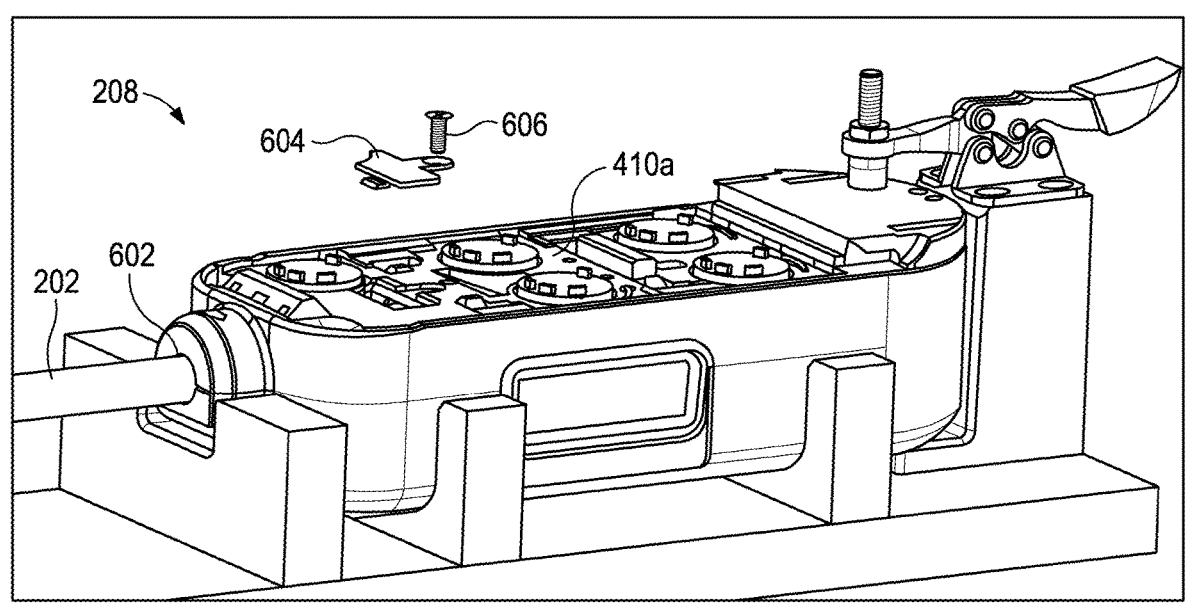
FIGS. 6A and 6B are enlarged isometric views of the drive housing of FIG. 2.
Figure 6B:
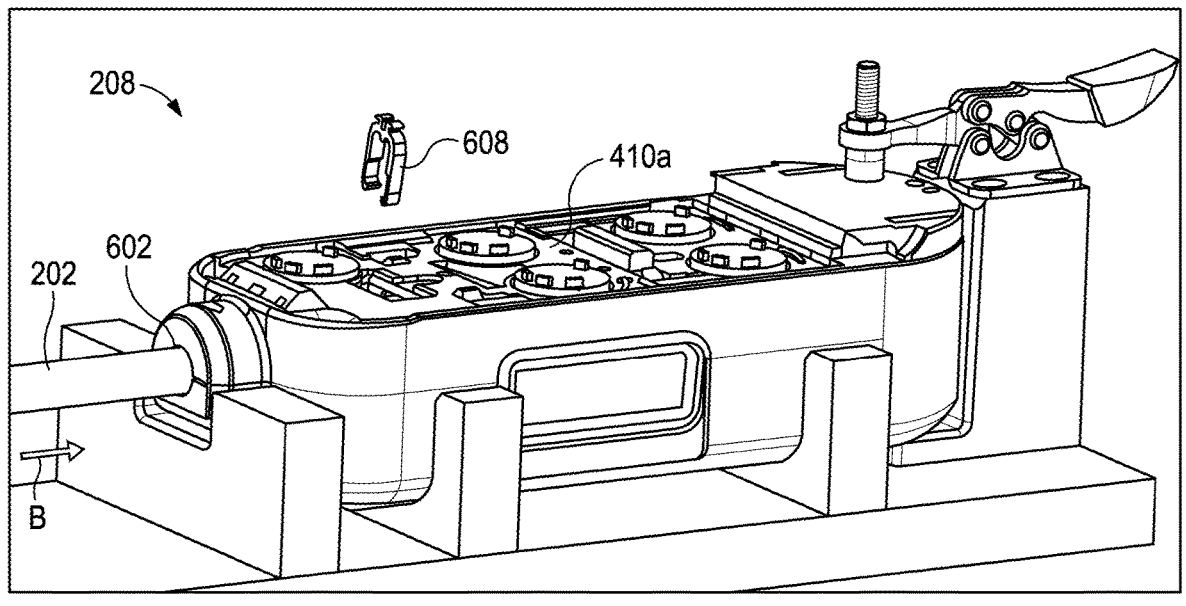

FIGS. 6A and 6B are enlarged isometric views of the drive housing 208. More specifically, FIGS. 6A-6B depict progressive steps to free the proximal end of the shaft 202, thereby allowing the shaft 202 to move in the proximal direction B and deeper into the interior of the drive housing 208. As illustrated, the shaft 202 extends through an aperture 602 defined in the drive housing 208 and extends into the interior of the drive housing 208. The proximal end of the shaft 202 may be secured within the interior the drive housing 208 such that the shaft 202 is prevented from translating axially in either direction (distally or proximally). In order to shift the shaft 202 in the proximal direction B, as discussed above with reference to FIG. 5B, the proximal end of the shaft 202 must first be freed from engagement with the drive housing 208

In some embodiments, an access panel or "carriage cover" 604 may be provided on the bottom portion 410a of the drive housing 208. In at least one embodiment, as illustrated, the carriage cover 604 may be mechanically fastened to the bottom portion 410 using one or more mechanical fasteners 606 (one shown). Once the carriage cover 604 is removed, a technician can access the interior the drive housing 208 and, specifically, the portion of the shaft 202 that needs to be disengaged to allow the shaft 202 to move in the proximal direction B.

Referring to FIG. 6B, one or more retention clips 608 (one shown) may be mounted within the interior of the drive housing 208 and configured to secure the shaft 202 at a distal position. Removing the carriage cover 604 may allow a technician to access the retention clip 608. Once the retention clip 608 is removed, the shaft 202 may be able to move in the proximal direction B. In the illustrated embodiment, the retention clip 608 comprises a type of C-clip or U-clip capable of extending partially around another object, such as the shaft 202 or a structure adjacent the shaft 202 and able to interact with the shaft 202, such as a shaft collar. When the shaft 202 is in its distal-most position, as shown in FIGS. 2, 4, and 5A, the retention clip 608 may be arranged to abut or engage a portion of the shaft 202, thereby preventing the shaft 202 from moving in the proximal direction B.

To be able to move the shaft 202 proximally B, as described in the process outlined in FIGS. 5A and 5B above, the retention clip 608 must either be removed or flexed out of engagement with the proximal end of the shaft 202. In embodiments, where the retention clip 608 comprises a C-clip, a U-clip or the like, the retention clip 608 may be manually removed by a technician and otherwise flexed out of engagement with the shaft 202. Those skilled in the art, however, will readily recognize that the retention clip 608 may comprise other types of mechanical components or devices capable of securing the shaft 202 in its distal-most position, without departing from the scope of the disclosure.

Figure 6C:
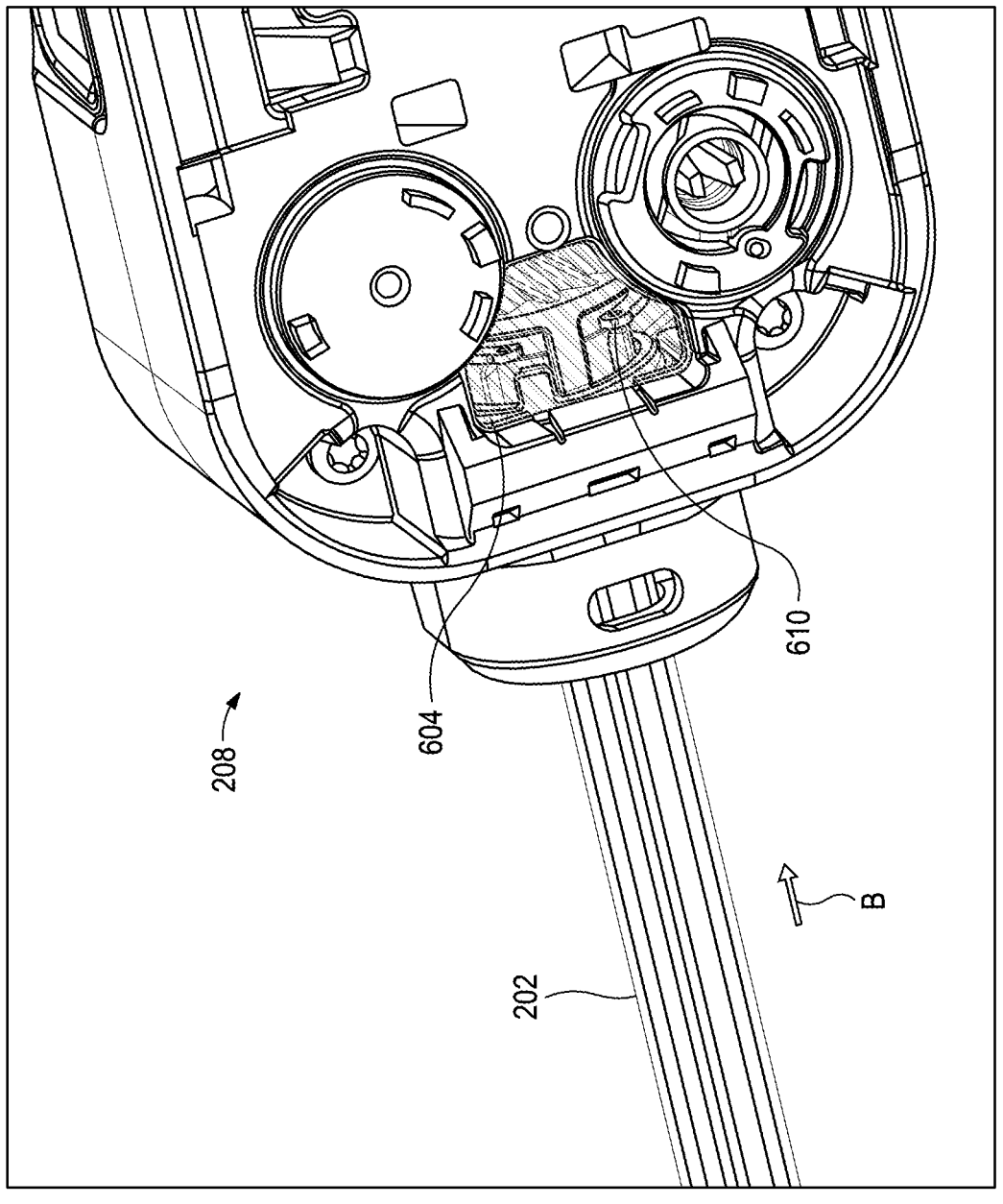
FIG. 6C is a bottom view of the drive housing, according to one or more additional embodiments.

FIG. 6C is an enlarged bottom view of the drive housing 208, according to one or more additional embodiments. In FIG. 6C, the carriage cover 604 is shown in phantom (dashed lines), thereby exposing a retention clip 610 arranged within the interior of the drive housing 208. The retention clip 610 may be similar in some respects to the retention clip 608 of FIG. 6B. For example, similar to the retention clip 608, the retention clip 610 may comprise a C-clip, a U-clip, or the like. Moreover, the retention clip 610 may be configured to extend at least partially about the outer circumference of the shaft 202 and thereby secure the shaft 202 at a distal position. Furthermore, removing the retention clip 610 from engagement with the shaft 202 may allow the shaft 202 to move in the proximal direction B. Unlike the retention clip 608, however, the retention clip 610 may not need to be removed entirely from the interior of the drive housing 208. Rather, the retention clip 610 need only be slightly opened and flexed out of engagement with the shaft 202 by a technician, which enables the shaft 202 to be moved proximally B and further into the interior of the drive housing 208.

Figure 7A:
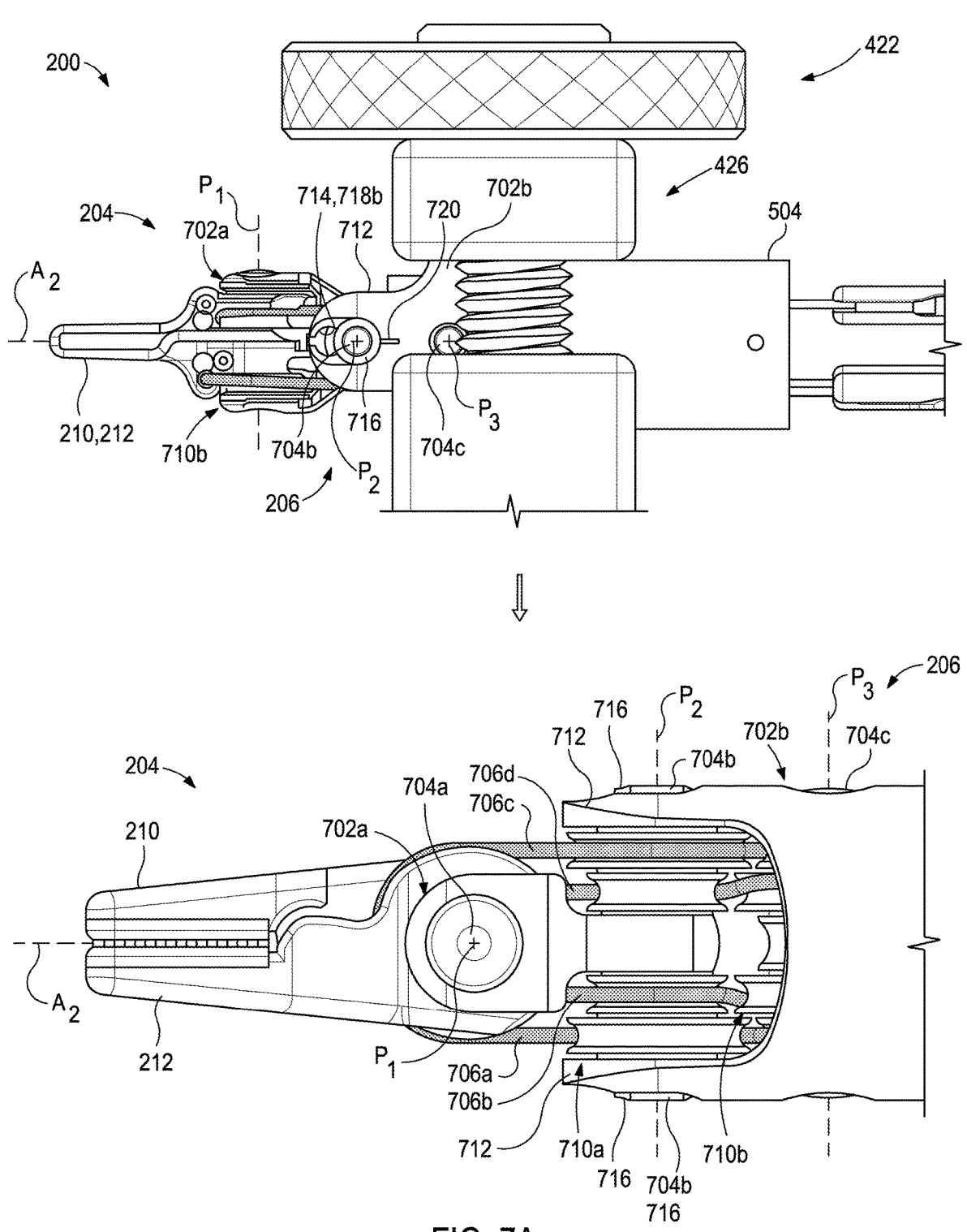
FIGS. 7A and 7B are enlarged views of the distal end of the surgical tool of FIGS. 2 and 4, according to one or more embodiments.
Figure 7B:
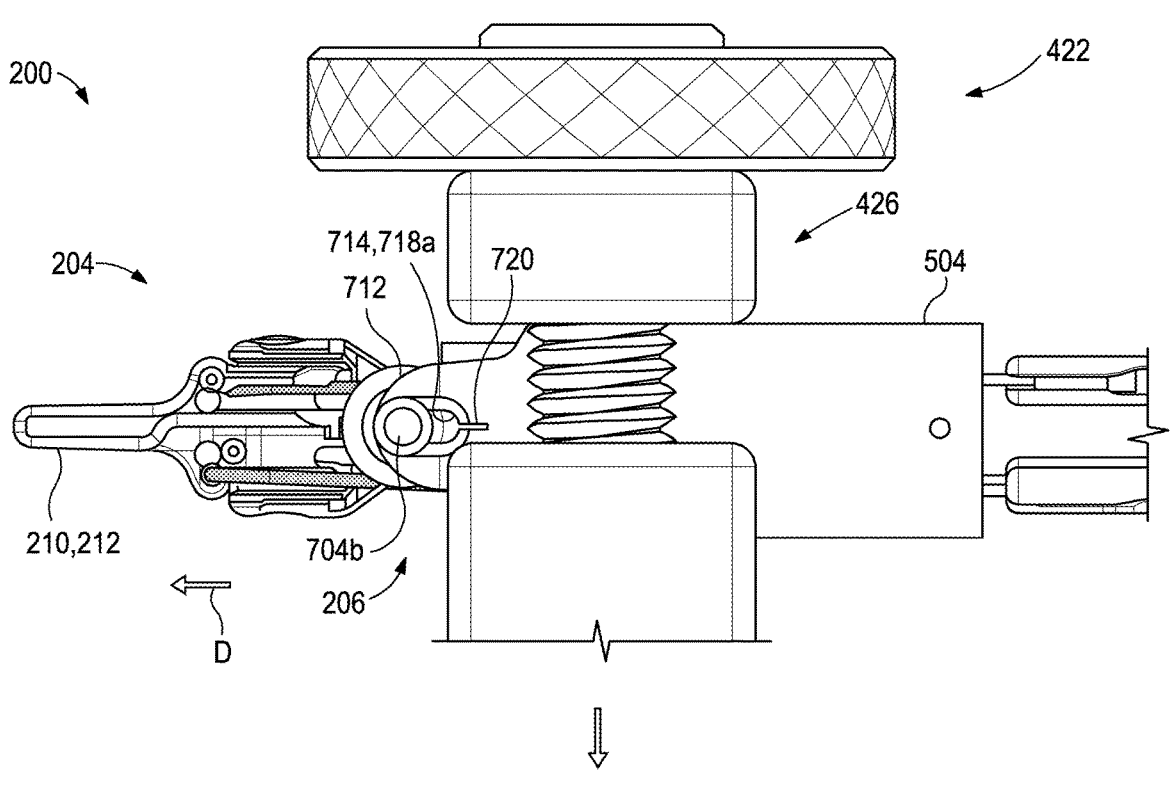
Figure 7B:
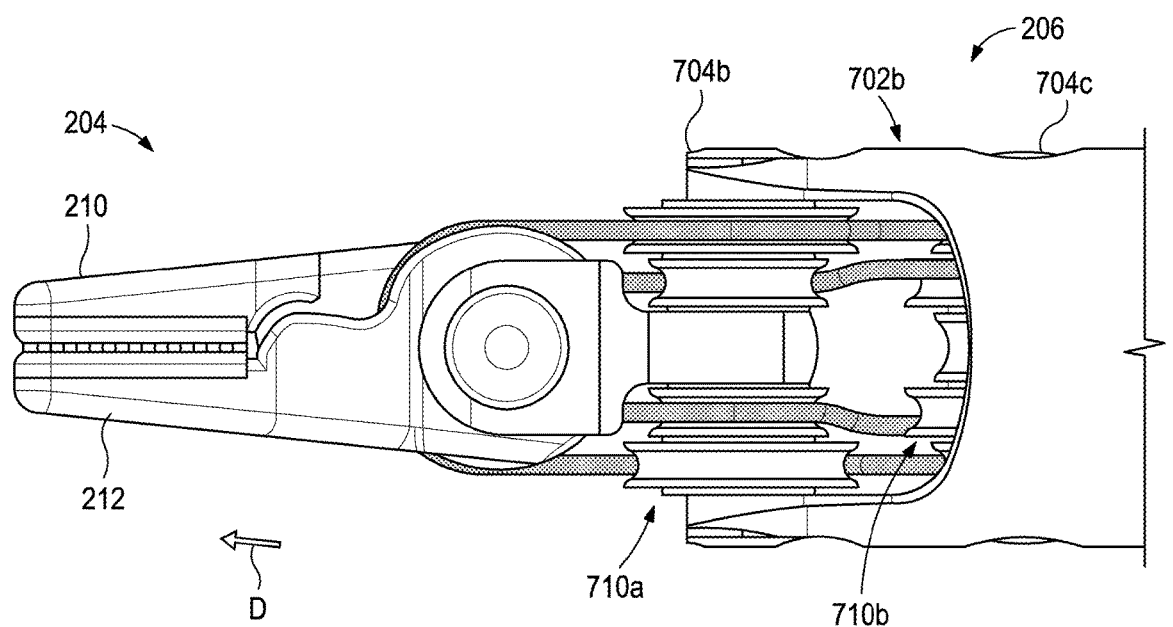

FIGS. 7A and 7B are enlarged views of the distal end of the surgical tool 200, according to one or more embodiments. More specifically, FIGS. 7A-7B are enlarged views of the end effector 204 and the wrist 206 and include corresponding upper and lower images, where the upper image is a side view of the end effector 204 and the wrist 206, and the lower image is rotated 90° to provide a top view of the same. Moreover, the upper image includes the end effector mount 422, and the securing mechanism 426 is shown clamped down against a portion of the wrist 206, which interposes the end effector 204 and the proximal clevis sleeve 504. In FIGS. 7A-7B, the shaft 202 has been removed from the proximal clevis sleeve 504, as generally described above with reference to FIGS. 5A-5B, and the end effector 204 is shown in the unarticulated position where the jaws 210, 212 are closed.

FIGS. 7A-7B also show progressive manipulation of the end effector 204 relative to the wrist 206, in accordance with the disassembly procedures described herein. More particularly, FIG. 7A shows the end effector 204 in a first or "assembled" state, where the end effector 204 is operationally mounted to the wrist 206, and FIG. 7B shows the end effector 204 moved distally to a second or "extended" state.

Referring first to FIG. 7A, the wrist 206 operatively couples the end effector 204 to the shaft 202, and in the illustrated embodiment, to the proximal clevis sleeve 504, which couples to the shaft 202 as generally described above. To accomplish this, the wrist 206 includes a distal clevis 702a and a proximal clevis 702b. The end effector 204 (i.e., the jaws 210, 212) is rotatably mounted to the distal clevis 702a at a first axle 704a (lower image), the distal clevis 702a is rotatably mounted to the proximal clevis 702b at a second axle 704b (upper image), and the proximal clevis 702b is coupled to the proximal clevis sleeve 504 (upper image). In the illustrated depiction, the securing mechanism 426 is clamped down against the proximal clevis 702b to secure the wrist 206 and the end effector 204 to the end effector mount 422. In other embodiments, however, the securing mechanism 426 may be clamped down against other portions of the wrist 206, without departing from the scope of the disclosure.

The wrist 206 provides a first pivot axis $P_1$ that extends through the first axle 704a and a second pivot axis $P_2$ that extends through the second axle 704b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 204, and movement about the second pivot axis $P_2$ provides "pitch" articulation of the end effector 204. In the illustrated embodiment, the jaws 210, 212 are mounted at the first pivot axis $P_1$, thereby allowing the jaws 210, 212 to pivot relative to each other to open and close the end effector 204 or alternatively pivot in tandem to articulate the orientation of the end effector 204.

As best seen in the lower image of FIG. 7A, a plurality of drive cables, shown as drive cables 706a, 706b, 706c, and 706d, extend proximally from the end effector 204 and extend through the wrist 206. The drive cables 706a-d may form part of the cable driven motion system housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive cables 706a-d can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof. While four drive cables 706a-d are depicted in FIG. 6B, more or less than four may be employed, without departing from the scope of the disclosure.

The drive cables 706a-d extend from the end effector 204 toward the drive housing 208 (FIGS. 2 and 4) where they are operatively coupled to various actuation mechanisms or devices that facilitate longitudinal movement (translation) of the drive cables 706a-d. Selective actuation of the drive cables 706a-d at the drive housing 208 applies tension (i.e., pull force) to the given drive cable 706a-d in the proximal direction, which urges the given drive cable 706a-d to translate longitudinally. More specifically, selective actuation causes a corresponding drive cable 706a-d to translate longitudinally and thereby cause pivoting movement of the end effector 204. One or more drive cables 706a-d, for example, may translate longitudinally to cause the end effector 204 to articulate (e.g., both of the jaws 210, 212 angled in a same direction), to cause the end effector 204 to open (e.g., one or both of the jaws 210, 212 move away from the other), or to cause the end effector 204 to close (e.g., one or both of the jaws 210, 212 move toward the other).

Moving the drive cables 706a-d can be accomplished in a variety of ways, such as by triggering an associated actuator or mechanism operatively coupled to or housed within the drive housing 208 (FIGS. 2 and 4). Moving a given drive cable 706a-d constitutes applying tension (i.e., pull force) to the given drive cable 706a-d in a proximal direction, which causes the given drive cable 706a-d to translate and thereby cause the end effector 204 to move (articulate) relative to the shaft 602.

As best seen in the lower image of FIG. 7A, the wrist 206 includes a first set of pulleys 710a and a second plurality of pulleys 710b, each configured to interact with and redirect the drive cables 706a-d for engagement with the end effector 204. The first set of pulleys 710a is mounted to the proximal clevis 702b at the second axle 704b and the second set of pulleys 710b is also mounted to the proximal clevis 702b but at a third axle 704c located proximal to the second axle 704b. The first and second sets of pulleys 710a,b cooperatively redirect the drive cables 706a-d through an "S" shaped pathway before the drive cables 706a-d are operatively coupled to the end effector 204.

In at least one embodiment, a pair of drive cables 706a-d is operatively coupled to each jaw 210, 212 and configured to "antagonistically" operate the corresponding jaw 210, 212. In the illustrated embodiment, for example, the first and second drive cables 706a,b may be coupled at the first jaw 210, and the third and fourth drive cables 706c,d may be coupled at the second jaw 212. Actuation of the first drive cable 706a acts on and pivots the first jaw 210 about the first pivot axis $P_1$ toward the open position. In contrast, actuation of the second drive cable 706b also acts on and pivots the first jaw 210 about the first pivot axis $P_1$ in the opposite direction and toward the closed position. Similarly, actuation of the third drive cable 706c acts and pivots the second jaw 212 about the first pivot axis $P_1$ toward the open position, while actuation of the fourth drive cable 706d also acts on but pivots the second jaw 212 about the first pivot axis $P_1$ in the opposite direction and toward the closed position.

Accordingly, the drive cables 706a-d may be characterized or otherwise referred to as "antagonistic" cables that cooperatively (yet antagonistically) operate to cause relative or tandem movement of the first and second jaws 210, 212. When the first drive cable 706a is actuated (moved), the second drive cable 706b naturally follows as coupled to the first drive cable 706a, and vice versa. Similarly, when the third drive cable 706c is actuated, the fourth drive cable 706d naturally follows as coupled to the third drive cable 706c, and vice versa.

Moreover, coordinated actuation of the drive cables 706a-d may also articulate the end effector 204 about the second pivot axis $P_2$. Consequently, the end effector 204 can articulate with multiple degrees of freedom, e.g., a degree of freedom by articulating about the first pivot axis $P_1$ and another degree of freedom by articulating about the second pivot axis $P_2$. The wrist 206 in this embodiment is pivotable about the second pivot axis $P_2$ in a single plane, e.g., in one of pitch and yaw, and the end effector 204 is pivotable about the first pivot axis $P_1$ in a single, different plane, e.g., the other of pitch and yaw.

As best seen in the lower image of FIG. 7A, the proximal clevis 702b provides opposing first and second arms 712 laterally offset from each other and extending distally toward the end effector 204. A gap (space) is formed between the arms 712 to receive the first and second sets of pulleys 710a,b and also to provide space to potentially accommodate the other elements of the end effector 204 that pass through the wrist 206 and extend to the end effector 204. As best seen in the upper image of FIG. 7A, in some embodiments, each arm 712 may provide and otherwise define an open-ended slot 714 (only one visible in FIG. 7A) open in the distal direction. Each open-ended slot 714 may comprise a portion of the proximal clevis 702b where the material of the proximal clevis 702b does not encircle (circumscribe) the second pivot axis $P_2$ (e.g., the "pitch" axis).

Each open-ended slot 714 may be configured to receive and seat a corresponding retaining cap or "end cap" 716 secured to the opposing ends of the second axle 704b. In some embodiments, the end caps 716 may form an integral part of the second axle 704b. In other embodiments, however, the end caps 716 may each comprise separate component parts configured to be operatively coupled to the opposing ends of the second axle 704b and configured to help secure the first set of pulleys 710a to the proximal clevis 702b.

Referring now to both FIGS. 7A-7B, since each slot 714 is open-ended in the distal direction, the end effector 204 may be pulled in the distal direction during disassembly, as shown by the arrow C, thereby transitioning the end effector 204 from the assembled state, as shown in FIG. 7A, to the extended state, shown in FIG. 7B. The slot 714 defined in the arms 712 provides and otherwise defines a first aperture 718a (FIG. 7B) and a second aperture 718b (FIG. 7A), where the first aperture 718a is located proximal to the second aperture 718b but contiguous therewith via a smaller portion (reduced section) of the slot 714. As illustrated, each arm 712 may also provide and otherwise define a slit 720 that is contiguous with the slot 714, but extends longitudinally away from the slot 714 in the proximal direction. The slit 720 introduces a point of weakness to each arm 712, thereby allowing opposing portions of each arm 712 to flex as the second axle 704b moves between the first aperture 718a and the second aperture 718b, and otherwise as the end effector 204 moves from the assembled state to the extended state.

FIG. 7A depicts the end effector 204 in the assembled state, where the second axle 704b is received within the first aperture 718a, and FIG. 7B depicts the end effector 204 in the extended state, where the second axle 704b is moved distally D and received within the second aperture 718b. A technician can move the end effector 204 to the extended state by manually moving the end effector 204 in the distal direction D. As the end effector 204 moves distally D, the second axle 704b moves (transitions) from the first aperture 718a to the second aperture 718b, and the first set of pulleys 710a correspondingly move distally away from the second set of pulleys 710b, which remain mounted to the proximal clevis 702b at the third axle 704c. Moving the second axle 704b from the first aperture 718a to the second aperture 718b correspondingly moves the first pulley set 710a distally, which enables the drive cables 706a-d to be both unthreaded and re-threaded through the pulley sets 710a and 710b with both the distal and proximal crimps on the drive cables 706a-d. This may prove advantageous in eliminating the need for a regional service center to have to do any crimping (i.e., the drive cables will arrive at the regional service center without any needs for crimping).

To enable the end effector 204 to be pulled distally, the surgical tool 200 (FIG. 2) may provide or otherwise incorporate slack into the design at the drive housing 208 (FIGS. 2 and 4). In such embodiments, for example, the drive cables 706a-d may each be configured to payout slack as the end effector 204 is pulled distally in the direction D. In at least one embodiment, this can be accomplished for the drive cables 706a-d by rotating the input capstans to unspool or payout cable through various spooling capstan mechanisms.

Figure 7C:
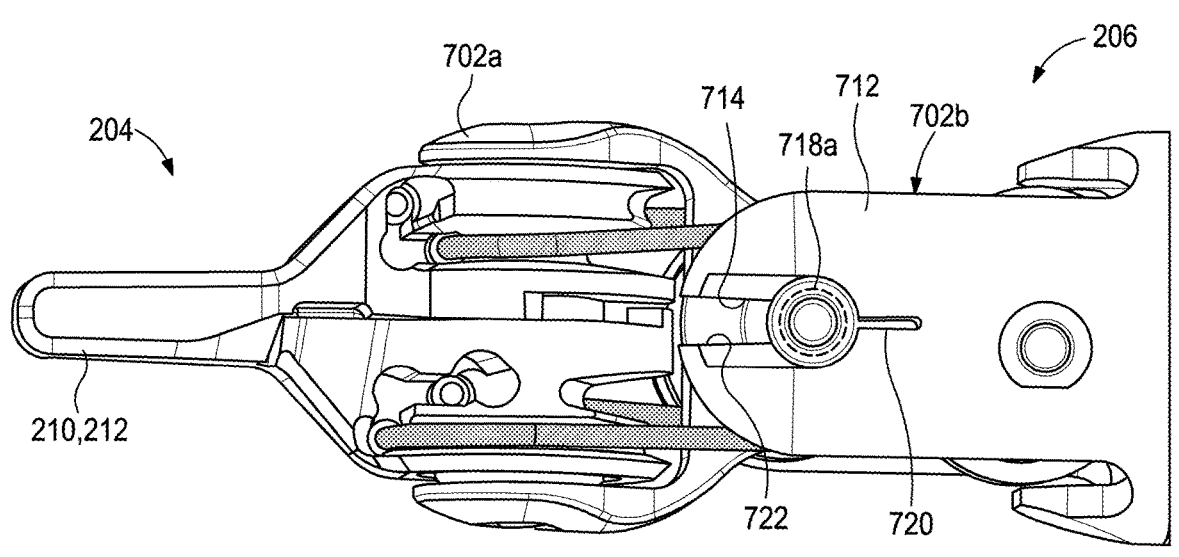
FIG. 7C is an enlarged side view of another embodiment of the end effector and the wrist, according to one or more additional embodiments.

FIG. 7C is an enlarged side view of another example of the end effector 204 and the wrist 206, according to one or more additional embodiments. As illustrated, the arm 712 of the proximal clevis 702b includes an alternative embodiment of the open-ended slot 714 that opens in the distal direction. Similar to the embodiment of the open-ended slot 714 provided in FIGS. 7A-7B, the slit 720 is contiguous with the open-ended slot 714 and extends proximally therefrom to allow opposing portions of the arm 712 to flex radially outward as the second axle 704b moves from the assembled state to the extended state.

In the illustrated embodiment, the open-ended slot 714 includes the first aperture 718a (shown in dashed lines), but omits the second aperture 718b (FIG. 7A). Instead, as the second axle 704b escapes the first aperture 718a, the second axle 704B may enter a substantially planar or straight section 722 of the open-ended slot 714. This allows the distal clevis 702a and the jaws 210, 212 to be moved even more distally to make it easier to replace the drive cables 706a-d. In addition, this also enables easy replacement of the distal clevis 702a and the jaws 210, 212 if they were damaged or worn.

Figure 8:
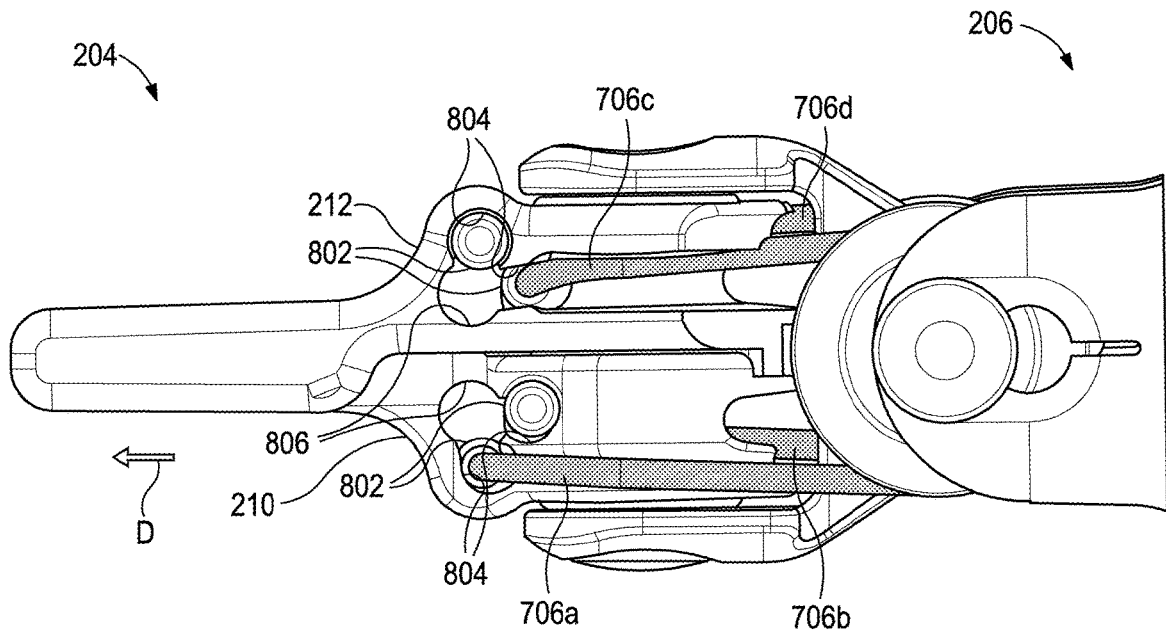
FIG. 8 is an enlarged view of the end effector moved to the extended state, according to one or more embodiments.

FIG. 8 is an enlarged view of the end effector 204 moved to the extended state, according to one or more embodiments. As illustrated, each drive cable 706a-d terminates at the end effector 204. More specifically, as mentioned above, the first and second drive cables 706a,b may terminate at the first jaw 210, and the third and fourth drive cables 706c,d may terminate at the second jaw 212. Moreover, each drive cable 706a-d may include a first or "distal" crimp 802 secured to its distal end, and each distal crimp 802 may be configured to be received within a corresponding counterbore 804 defined in a corresponding one of the first and second jaws 210, 212. More particularly, the first jaw 210 may provide and otherwise defined two counterbores 804 configured to receive the distal crimps 802 secured to the distal ends of the first and second drive cables 706a,b, and the second jaw 212 may provide and otherwise define an additional two counterbores 804 configured to receive the distal crimps 802 secured to the distal ends of the third and fourth drive cables 706c,d.

Each jaw 210, 212 may further provide and otherwise define a common aperture 806 that is contiguous with the counterbores 804 defined in the corresponding jaw 210, 212. The diameter of the common aperture 806 is larger than the diameter of each distal crimp 802, and thereby provides a means to assemble the distal crimps 802 to the corresponding counterbores 804, but also provides a means to remove the distal crimps 802 from the counterbores 804 during disassembly.

More specifically, to receive a distal crimp 802 within a corresponding counterbore 804, the distal crimp 802 may first be inserted through or otherwise received within the common aperture 806, following which the corresponding drive cable 706a-d may be threaded into the counterbore 804. Once the drive cable 706a-d is threaded into the counterbore 804, the drive cable 706a-d may be retracted to seat the corresponding distal crimp 802 within the associated counterbore 804. Disassembly or removal of the distal crimp 802 from the counterbore 804 may be accomplished by reversing the foregoing process. Once each of the distal crimps 802 are successfully removed from the corresponding counterbores 804, the end effector 204 may be separated from portions of the wrist 206 by manually pulling in the distal direction D. The common aperture 806 may prove advantageous in allow the drive cables 706ad to be replaced at a service center with the distal crimps 802 and proximal crimps (as discussed below) on both ends of the drive cables 706a-d. This eliminates the need for crimping at the service center.

Figure 9A:
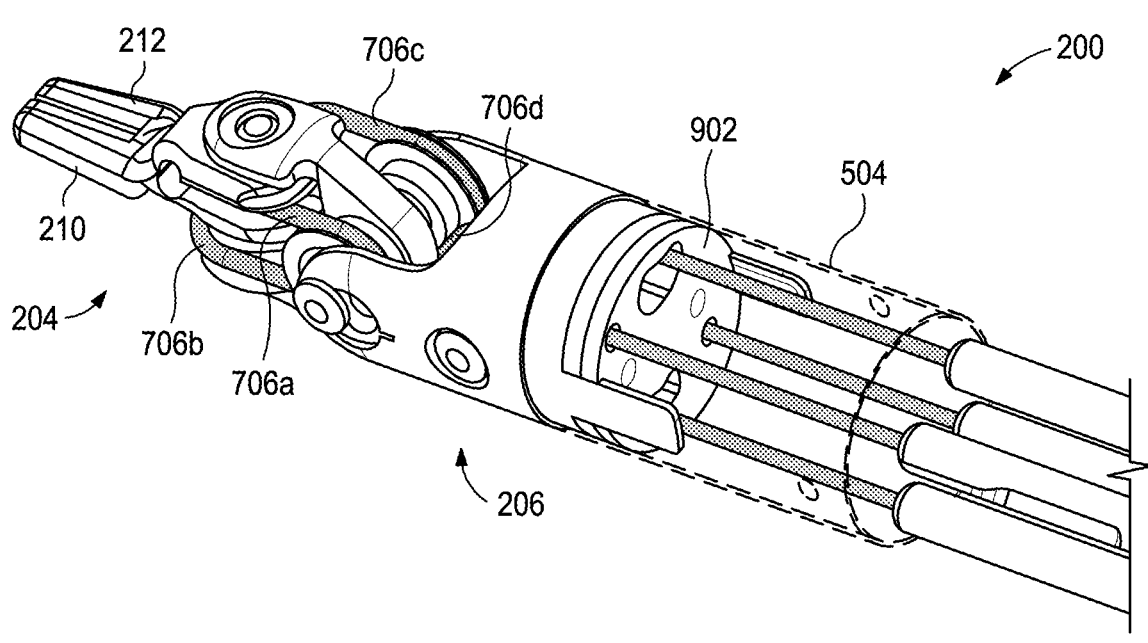
FIGS. 9A and 9B are isometric views of the distal end of the surgical tool showing progressive steps of disassembly, according to embodiments of the present disclosure.
Figure 9B:
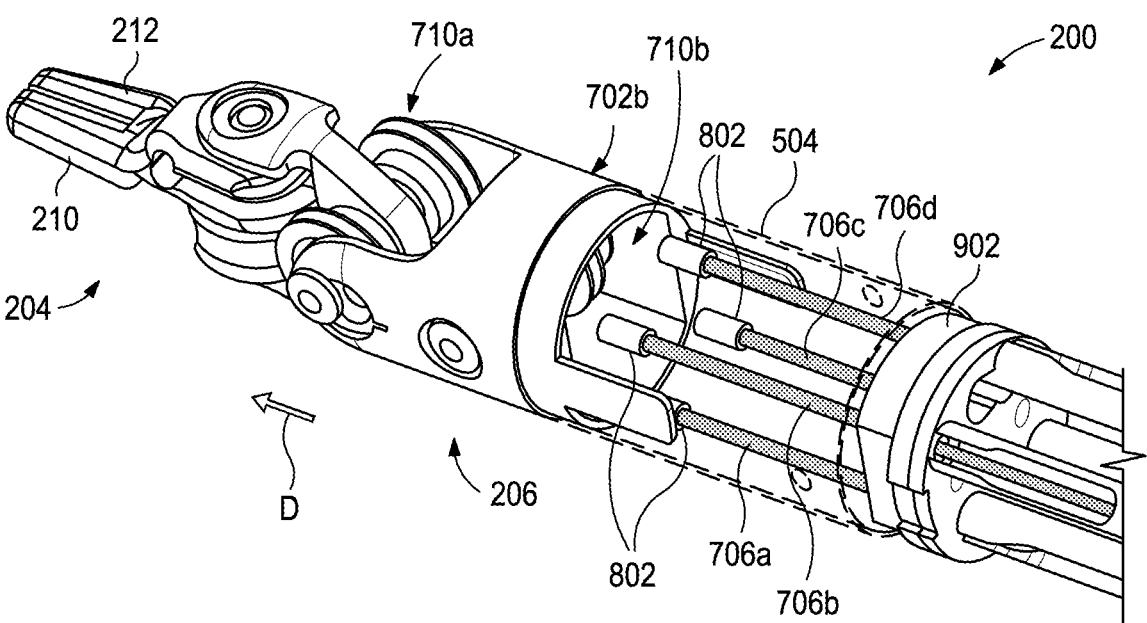

FIGS. 9A and 9B are isometric views of the distal end of the surgical tool 200 showing additional progressive steps of disassembly, according to embodiments of the present disclosure. More particularly, 9A-9B show progressive disassembly of the end effector 204 and the wrist 206 from proximal portions of the surgical 200.

In FIG. 9A, the drive cables 706a-d are coupled to the end effector 204, as generally described above, where the distal crimps 802 (FIG. 8) are received within the corresponding counterbores 804 (FIG. 8) of each jaw 210, 212. As illustrated, the drive cables extend through the wrist, which includes a distal seal assembly 902 arranged at least partially within the proximal clevis sleeve 504 (shown in dashed lines). The distal seal assembly 902 may comprise a generally cylindrical structure sized to be received within the interior of the proximal clevis sleeve 504 and defining a plurality of apertures that extend axially therethrough to accommodate the drive cables 706a-d as they extend to the end effector 204. In example operation, the distal seal assembly 902 may be configured to allow pressure to be maintained with the abdomen of the patient (i.e., provides a gas seal) to create abdominal space to perform a procedure laparoscopically. The distal seal assembly 902 also minimizes the amount of patient fluid and tissue entering the shaft 202 (FIG. 2), which makes it easier to clean the device for the subsequent patient.

In FIG. 9B, the distal crimps 802 are shown detached from the corresponding jaws 210, 212, in the disassembly process generally described with reference to FIG. 8 above. After detaching the distal crimps 802 from the corresponding jaws 210, 212, the distal crimps 802 may be fished through the first and second sets of pulleys 710a,b rotatably mounted to the proximal clevis 702b. The distal end of the surgical tool 200 may then be removed from proximal portions of the surgical tool 200. More specifically, the end effector 204 and the wrist 206 may be manually moved in the distal direction D, which may allow the distal seal assembly 902 to exit the proximal clevis sleeve 504, thereby effectively detaching the end effector 204 and the wrist 206 from proximal portions of the surgical tool 200.

At this point, if desired, the entire end effector 204 and the wrist 206, including all of the "consumables" or high-wear components pertaining to such components, may be replaced. In such embodiments, a new or refurbished end effector and/or wrist may be provided, and the foregoing steps of disassembly and detachment up to this point may be reversed to reattach the component parts to the remaining (proximal) portions of the surgical tool 200 (FIG. 2).

Alternatively, if it is desired to replace individual "consumables" pertaining to the end effector 204 or the wrist 206, the end effector 204 may undergo further disassembly. Example consumables of the end effector 204 that may be replaced by further disassembling the end effector 204 include, but are not limited to, the jaws 210, 212 (one or both), and example consumables of the wrist 206 that may be replaced include, but are not limited to, the first and second sets of pulleys 710*a,b*, the proximal clevis 702B, the proximal clevis sleeve 504, or any combination thereof.

Figure 10A:
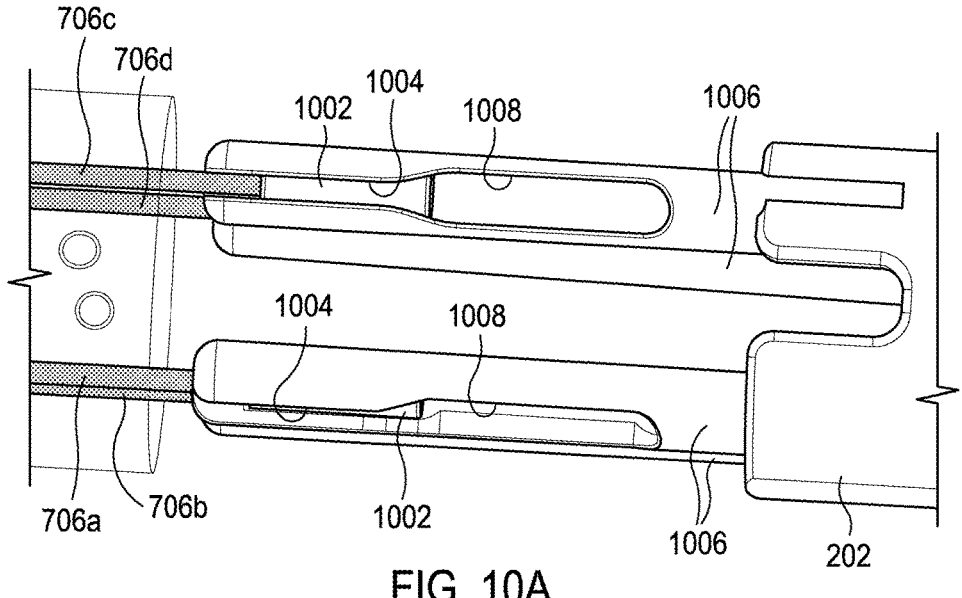
FIGS. 10A and 10B depict additional steps of disassembly, according to one or more additional embodiments of the present disclosure.
Figure 10B:
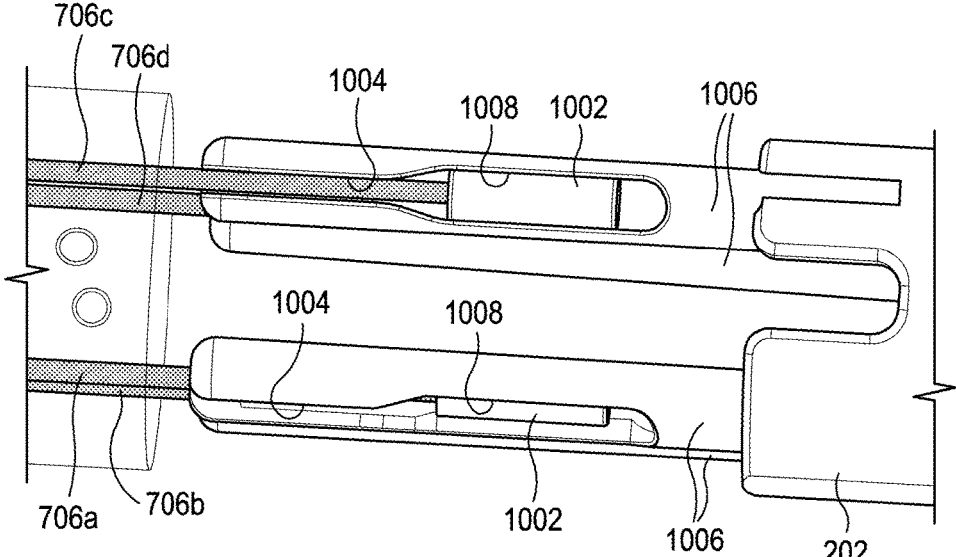

FIGS. 10A and 10B depict additional steps of disassembly, according to one or more additional embodiments of the present disclosure. More specifically, FIGS. 10A-10B depict one embodiment of the drive cable 706*a-d* where a proximal end of each drive cable 706*a-d* may include a second or "proximal" crimp 1002 secured thereto. In such embodiments, each proximal crimp 1002 may be configured to be received within a hypotube 1006 or an intermediate socket component that attaches to hypotube 1006 that extends into the shaft 202. Each hypotube 1006 may be coupled to a corresponding proximal extension of the drive cables 706*a-d* that extend to the drive housing 208 (FIGS. 2 and 4). In such embodiments, the drive cables 706*a-d* may be referred to and otherwise characterized as "distal cables", and the proximal extensions secured to each hypotube 1006 and extend to the drive housing 208 may be referred to as "proximal cables".

As illustrated, each hypotube 1006 includes a cable socket 1004, which provides a crimp opening 1008 that exhibits a diameter larger than the diameter of the proximal crimp 1002. Accordingly, the drive cables 706*a-d* (e.g., the "distal cables") may be secured to a corresponding hypotube 1006 by aligning the corresponding proximal crimp 1002 with the crimp opening 1008, receiving the proximal crimp 1002 within the cable socket 1004, and then pulling distally on the drive cable 706*a-d* to receive and seat the proximal crimp 1002 within the cable pocket 1004. Disassembly or removal of the proximal crimp 1002 from the cable socket 1004 may be accomplished by reversing the foregoing process.

Figure 11:
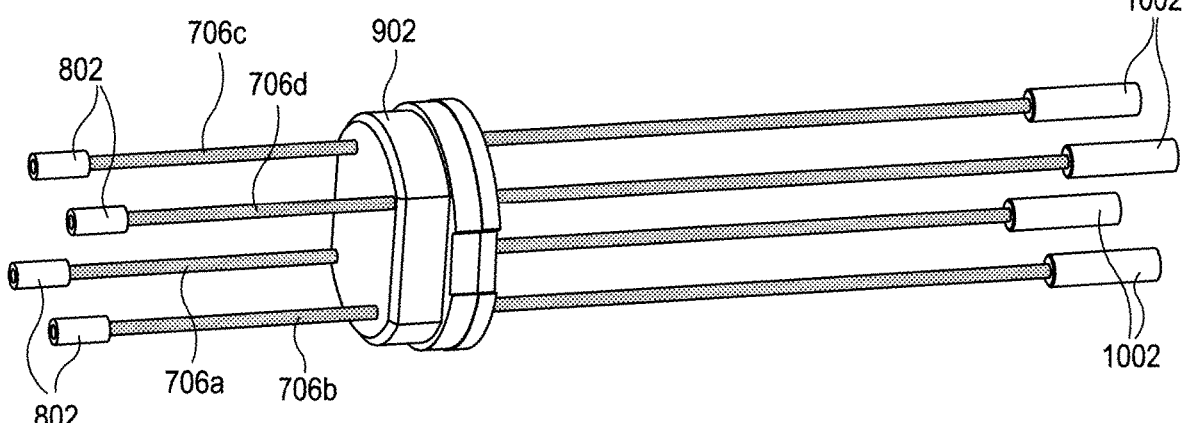
FIG. 11 is an isometric view of the drive cable and the distal seal assembly, according to one or more embodiments.

FIG. 11 is an isometric view of the drive cables 706*a-d* (e.g., the "distal cables") and the distal seal assembly 902, according to one or more embodiments. Once each of the distal crimps 802 are successfully detached (disassembled) from the jaws 210, 212, as generally described above with reference to FIGS. 9A-9B, and the proximal crimps 1002 are successfully removed from the corresponding cable sockets 1004, as generally described above with reference to FIGS. 10A-10B, the drive cables 706*a-d* and the distal seal assembly 902 may be replaced and/or refurbished. In such embodiments, the drive cables 706*a-d* and the distal seal assembly 902 may be characterized as "consumables".

The foregoing steps of disassembly and detachment of the surgical tool 200 (FIG. 2) up to this point may then be reversed to place the surgical tool 200 back into service. In particular, in a process that reverses the process outlined in FIGS. 10A-10B above, the proximal crimps 1002 of each drive cable 706*a-d* may be aligned with the crimp opening 1008 of a corresponding hypotube 1006, inserted into the cable socket 1004, and then the drive cables 706*a-d* may be pulled distally to receive and seat the proximal crimps 1002 within the corresponding cable pockets 1004.

Moreover, in a process that reverses the process outlined in FIGS. 9A-9B above, after the drive cables 706*a-d* are threaded through the second plurality of pulleys 710*b* and the distal seal assembly 902 located in the shaft adapter 504, the end effector 204 and the wrist 206 may be moved in the proximal direction B. The distal crimps 802 may then be fished through and otherwise threaded back through the first set of pulleys 710,*b* to be received at the corresponding jaws 210, 212.

In a process that reverses the process outlined in FIG. 8 above, the distal crimps 802 of each drive cable 706*a-d* may be mounted to the jaws 210, 212 of the end effector 204. More specifically, the distal crimps 802 may be inserted through or otherwise received within the corresponding common aperture 806, following which the corresponding drive cable 706*a-d* may be threaded into the counterbore 804. Once the drive cable 706*a-d* is threaded into the counterbore 804, the drive cable 706*a-d* may be retracted to seat the corresponding distal crimp 802 within the associated counterbore 804.

In a process that reverses the process outlined in FIGS. 7A-7B, the end effector 204 may be moved in the proximal direction B to correspondingly move the second axle 704*b* in the same direction within the open-ended slot 714 until returning to the assembled state. Moving the second axle 704*b* in the proximal direction B within open-ended slot 714 may cause the opposing portions of each arm 712 to flex radially outward. Moreover, moving the end effector 204 proximally B to the assembled state also moves the first set of pulleys 710*a* back toward the second set of pulleys 710*b* rotatably mounted to the proximal clevis 702*b* at the third axle 704*c*.

In a process that reverses the process outlined in FIGS. 5A-5B above, the shaft 202 may then be manually moved distally D and otherwise back toward the end effector 204. In such embodiments, the distal end of the shaft 202 may be received within the proximal clevis sleeve 504. In at least one embodiment, the shaft 202 is moved distally D until it bottoms out within the proximal clevis sleeve 504. In some embodiments, it may be necessary to apply the opposing radial loads C to the proximal clevis sleeve 504 to cause the proximal clevis sleeve 504 to flex radially outward at the location of the projections 508 and thereby assume a generally oval shape. This may help the projections 508 be received within the corresponding grooves 510 defined on the outer radial surface of the shaft 202.

Moreover, in a process that reverses the process outlined in FIGS. 6A-6B, once the shaft 202 reaches its distal position, the retention clip 608 (or the retention clip 610 of FIG. 6C) may be reinstalled within the interior of the drive housing 208 to secure the shaft 202 at the distal position. The carriage cover 604 may then be reinstalled and secured in place with the mechanical fastener 606.

Finally, in a process that reverses the process outlined in FIG. 4 above, the surgical tool 200 may be detached and removed from the disassembly fixture 402. The surgical tool 200 may then be cleaned and tested, then delivered to a distribution center and subsequently sent to an end user (e.g., a hospital, a surgeon, an operator, etc.) for further use.

Embodiments disclosed herein include:

A. A method of replacing a consumable of a surgical tool includes securing the surgical tool, the surgical tool including a drive housing, an elongate shaft extending distally from the drive housing, an end effector arranged at a distal end of the shaft and including opposing first and second jaws, a wrist interposing the distal end of the shaft and the end effector, and a plurality of drive cables extending proximally from the end effector and through the wrist. The method further including moving the shaft proximally away from the end effector and deeper into the drive housing, detaching the plurality of drive cables from the first and second jaws, displacing the end effector and the wrist distally from proximal portions of the surgical tool, replacing the consumable of the surgical tool, reconnecting the end effector and the wrist to the proximal portions of the surgical tool, reconnecting the plurality of drive cables to the first and second jaws, and moving the elongate shaft distally toward the wrist and the end effector.

B. A surgical tool configured for a circularity processing system includes a drive housing, an elongate shaft extending distally from the drive housing, an end effector arranged at a distal end of the shaft and including opposing first and second jaws, the first jaw defining a first counterbore and a first common aperture contiguous with the first counterbore, and the second jaw defining a second counterbore and a second common aperture contiguous with the second counterbore, a wrist interposing the distal end of the shaft and the end effector, and a plurality of drive cables extending proximally from the end effector and through the wrist, the plurality of drive cables including a first drive cable having a first distal crimp receivable within the first counterbore, and a second drive cable having a second distal crimp receivable within the second counterbore, wherein a diameter of the first common aperture is larger than a diameter of the first distal crimp, and wherein a diameter of the second common aperture is larger than a diameter of the second distal crimp.

C. A surgical tool configured for a circularity processing system includes a drive housing, an elongate shaft extending distally from the drive housing and having one or more grooves defined on an outer radial surface at or near a distal end of the shaft, an end effector arranged at the distal end of the shaft and including opposing first and second jaws, a wrist interposing the distal end of the shaft and the end effector, a proximal clevis sleeve operatively coupled to the wrist and operable to receive the distal end of the shaft, one or more projections being defined on an inner radial surface of the proximal clevis sleeve and receivable within the one or more grooves when the distal end of the shaft is received within the proximal clevis sleeve, wherein applying opposing radial loads on the proximal clevis sleeve dislodges the one or more projections from the one or more grooves and allows the shaft to move proximally away from the proximal clevis sleeve.

D. A surgical tool configured for a circularity processing system includes a drive housing, an elongate shaft extending distally from the drive housing, an end effector arranged at a distal end of the shaft and including opposing first and second jaws, a wrist interposing the shaft and the end effector and including a proximal clevis having opposing first and second arms laterally offset from each other and extending distally, each arm defining an open-ended slot that opens distally, and a set of pulleys rotatably mounted to the proximal clevis at an axle receivable within the open-ended slot of each arm, the set of pulleys being rotatable about a pivot axis extending through the axle, wherein material of the proximal clevis fails to encircle the pivot axis.

Each of embodiments A, B, C, and D may have one or more of the following additional elements in any combination: Element 1: wherein the surgical tool further includes a proximal clevis sleeve operatively coupled to the wrist and the distal end of the shaft is received within the proximal clevis sleeve, and wherein moving the elongate shaft proximally comprises applying opposing radial loads on opposite sides of the proximal clevis sleeve and thereby elastically deforming the proximal clevis sleeve, dislodging one or more projections defined on an inner radial surface of the proximal clevis sleeve from one or more corresponding grooves defined on an outer radial surface of the shaft when the proximal clevis sleeve elastically deforms, and moving the shaft proximally once the one or more projections are dislodged from the one or more corresponding grooves. Element 2: wherein the surgical tool further includes one or more retention clips provided within an interior of the drive housing and engageable with the shaft within the drive housing, and wherein moving the shaft proximally comprises accessing an interior of the drive housing, moving the one or more retention clips out of engagement with the shaft, and moving the shaft proximally and further into the interior of the drive housing. Element 3: wherein the wrist includes a proximal clevis having opposing first and second arms laterally offset from each other and extending distally, each arm defining an open-ended slot that opens distally, and the surgical tool further includes first and second sets of pulleys rotatably mounted to the proximal clevis at first and second axles, respectively, and wherein detaching the plurality of drive cables from the first and second jaws is preceded by moving the end effector distally relative to the wrist and thereby moving the first axle distally within the open-ended slots, and separating the first set of pulleys from the second set of pulleys as the first axle moves distally within the open-ended slots. Element 4: wherein each open-ended slot defines a first aperture and a second aperture contiguous with and located distal to the first aperture, and wherein moving the first axle distally within the open-ended slots comprises flexing opposing portions of each arm radially outward as the first axle moves distally within the open-ended slots and transitions from the first aperture to the second aperture. Element 5: wherein a distal crimp is secured to a distal end of each drive cable, and wherein detaching the plurality of drive cables from the first and second jaws comprises dislodging the distal crimp from a counterbore defined in a corresponding one of the first and second jaws, aligning the distal crimp with a common aperture contiguous with the counterbore, a diameter of the common aperture being larger than a diameter of the distal crimp, and advancing the distal crimp through the common aperture. Element 6: wherein the plurality of drive cables comprises first and second drive cables operatively coupled to the first jaw, and third and fourth drive cables operatively coupled to the second jaw, and wherein detaching the plurality of drive cables from the first and second jaws comprises dislodging distal crimps attached to distal ends of the first and second drive cables from first and second counterbores, respectively, defined in the first jaw, dislodging distal crimps attached to distal ends of the third and fourth drive cables from third and fourth counterbores, respectively, defined in the second jaw, aligning the distal crimps of the first and second drive cables with a first common aperture defined in the first jaw and contiguous with the first and second counterbores, a diameter of the first common aperture being larger than a diameter of the distal crimps of the first and second drive cables, aligning the distal crimps of the third and fourth drive cables with a second common aperture defined in the second jaw and contiguous with the third and fourth counterbores, a diameter of the second common aperture being larger than a diameter of the distal crimps of the third and fourth cables, advancing the distal crimps of the first and second drive cables thorough the first common aperture, and advancing the distal crimps of the third and fourth drive cables thorough the second common aperture. Element 7: wherein the surgical tool further includes a proximal clevis sleeve operatively coupled to the wrist and the distal end of the shaft is receivable within the proximal clevis sleeve, and a distal seal assembly arranged within the proximal clevis sleeve and through which the plurality of drive cables extend, and wherein removing the end effector and the wrist from proximal portions of the surgical tool comprises detaching the plurality of drive cables from the first and second jaws, pulling the plurality of drive cables through and out of engagement with the wrist, and moving the end effector and the wrist distally away from the proximal portions of the surgical tool and thereby removing the distal seal assembly from the proximal clevis sleeve. Element 8: wherein a proximal crimp is secured to a proximal end of each drive cable and the surgical tool further includes a plurality of hypotubes arranged within the shaft, each hypotube being configured to receive the proximal crimp of a corresponding one of the drive cables, the method further comprising detaching each proximal crimp from the plurality of hypotubes, and replacing at least one of the plurality of drive cables and the distal seal assembly, wherein the consumable comprises the at least one of the plurality of drive cables and the distal seal assembly. Element 9: wherein securing the surgical tool comprises mounting the surgical tool to a disassembly fixture, which includes the steps of mounting the drive housing to a drive housing mount of the disassembly fixture, and securing the end effector to an end effector mount of the disassembly fixture. Element 10: wherein the plurality of drive cables comprises first and second drive cables operatively coupled to the first jaw, and third and fourth drive cables operatively coupled to the second jaw, each drive cable having a distal crimp secured to a distal end and a proximal crimp secured to a proximal end, and wherein replacing the consumable of the surgical tool comprises replacing one or more of the plurality of drive cables.

Element 11: wherein the first jaw further defines a third counterbore continuous with the first common aperture and the second jaw further defines a fourth counterbore contiguous with the second common aperture, the plurality of drive cables further including a third drive cable having a third distal crimp receivable within the third counterbore, and a fourth drive cable having a fourth distal crimp receivable within the fourth counterbore, wherein the diameter of the first common aperture is larger than a diameter of the third distal crimp, and wherein the diameter of the second common aperture is larger than a diameter of the fourth distal crimp. Element 12: further comprising a proximal clevis sleeve operatively coupled to the wrist and operable to receive the distal end of the shaft, one or more grooves defined on an outer radial surface of the shaft, and one or more projections defined on an inner radial surface of the proximal clevis sleeve and receivable within the one or more grooves when the distal end of the shaft is received within the proximal clevis sleeve, wherein applying opposing radial loads on the proximal clevis sleeve dislodges the one or more projections from the one or more grooves. Element 13: further comprising one or more retention clips provided within an interior of the drive housing and engageable with the shaft within the drive housing, wherein disengaging the one or more retention clips from the shaft allows the shaft to move proximally and further into the interior of the drive housing. Element 14: wherein the wrist includes a proximal clevis having opposing first and second arms laterally offset from each other and extending distally, each arm defining an open-ended slot that opens distally, a first set of pulleys rotatably mounted to the proximal clevis at a first axle, a second set of pulleys rotatably mounted to the proximal clevis at a second axle located proximal to the first axle. Element 15: further comprising a proximal clevis sleeve operatively coupled to the wrist and operable to receive the distal end of the shaft, a distal seal assembly arranged within the proximal clevis sleeve and through which the plurality of drive cables extend, a proximal crimp secured to a proximal end of each drive cable, and a plurality of hypotubes arranged within the shaft and configured to receive the proximal crimp of a corresponding one of the drive cables, wherein the plurality of drive cables and the distal seal assembly are removable from the proximal clevis sleeve and the wrist.

Element 16: further comprising one or more retention clips provided within an interior of the drive housing and engageable with the shaft within the drive housing, wherein disengaging the one or more retention clips from the shaft allows the shaft to move proximally and further into the interior of the drive housing. Element 17: wherein the wrist includes a proximal clevis having opposing first and second arms laterally offset from each other and extending distally, each arm defining an open-ended slot that opens distally, a first set of pulleys rotatably mounted to the proximal clevis at a first axle, a second set of pulleys rotatably mounted to the proximal clevis at a second axle located proximal to the first axle. Element 18: wherein each open-ended slot defines a first aperture and a second aperture contiguous with and located distal to the first aperture, and wherein moving the first axle distally within the open-ended slots causes opposing portions of each arm to flex as the first axle moves from the first aperture to the second aperture.

Element 19: wherein each open-ended slot defines a first aperture and a second aperture contiguous with and located distal to the first aperture, and wherein moving the axle distally within the open-ended slots causes opposing portions of each arm to flex as the axle moves from the first aperture to the second aperture. Element 20: wherein the set of pulleys comprises a first set of pulleys and the axle comprises a first axle, the surgical tool further comprises a second set of pulleys rotatably mounted to the proximal clevis at a second axle located proximal to the first axle, and wherein moving the first axle distally within the open-ended slots from the first aperture to the second aperture transitions the end effector from an assembled state to an extended state where the first axle is moved distally from the second axle.

By way of non-limiting example, exemplary combinations applicable to A, B, C, and D include: Element 3 with Element 4; Element 7 with Element 8; Element 17 with Element 18; and Element 20 with Element 21.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, uphole, downhole and the like are used in relation to the illustrative embodiments as they are depicted in the figures, the upward direction being toward the top of the corresponding figure and the downward direction being toward the bottom of the corresponding figure.

What is claimed is:

1. A method of replacing a consumable of a surgical tool, comprising:
   securing the surgical tool, the surgical tool including:
      a drive housing;
      an elongate shaft extending distally from an interior of the drive housing;
      an end effector arranged at a distal end of the elongate shaft and including opposing first and second jaws;
      a wrist interposing the distal end of the elongate shaft and the end effector; and
      a plurality of drive cables extending proximally from the end effector and through the wrist;
   moving the elongate shaft proximally away from the end effector and deeper into the interior of the drive housing;
   detaching the plurality of drive cables from the first and second jaws;
   displacing the end effector and the wrist distally from proximal portions of the surgical tool;
   replacing the consumable of the surgical tool;

reconnecting the end effector and the wrist to the proximal portions of the surgical tool;
reconnecting the plurality of drive cables to the first and second jaws; and
moving the elongate shaft distally toward the wrist and the end effector.

2. The method of claim 1, wherein the surgical tool further includes a proximal clevis sleeve operatively coupled to the wrist and the distal end of the elongate shaft is received within the proximal clevis sleeve, and wherein moving the elongate shaft proximally comprises:
   applying opposing radial loads on opposite sides of the proximal clevis sleeve and thereby elastically deforming the proximal clevis sleeve;
   dislodging one or more projections defined on an inner radial surface of the proximal clevis sleeve from one or more corresponding grooves defined on an outer radial surface of the elongate shaft when the proximal clevis sleeve elastically deforms; and
   moving the elongate shaft proximally once the one or more projections are dislodged from the one or more corresponding grooves.

3. The method of claim 1, wherein the surgical tool further includes one or more retention clips provided within an interior of the drive housing and engageable with the elongate shaft within the drive housing, and wherein moving the elongate shaft proximally comprises:
   accessing an interior of the drive housing;
   moving the one or more retention clips out of engagement with the elongate shaft; and
   moving the elongate shaft proximally and further into the interior of the drive housing.

4. The method of claim 1, wherein the wrist includes a proximal clevis having opposing first and second arms laterally offset from each other and extending distally, each arm defining an open-ended slot that opens distally, and the surgical tool further includes first and second sets of pulleys rotatably mounted to the proximal clevis at first and second axles, respectively, and
   wherein detaching the plurality of drive cables from the first and second jaws is preceded by:
   moving the end effector distally relative to the wrist and thereby moving the first axle distally within the open-ended slots; and
   separating the first set of pulleys from the second set of pulleys as the first axle moves distally within the open-ended slots.

5. The method of claim 4, wherein each open-ended slot defines a first aperture and a second aperture contiguous with and located distal to the first aperture, and wherein moving the first axle distally within the open-ended slots comprises flexing opposing portions of each arm radially outward as the first axle moves distally within the open-ended slots and transitions from the first aperture to the second aperture.

6. The method of claim 1, wherein a distal crimp is secured to a distal end of each drive cable, and wherein detaching the plurality of drive cables from the first and second jaws comprises:
   dislodging the distal crimp from a counterbore defined in a corresponding one of the first and second jaws;
   aligning the distal crimp with a common aperture contiguous with the counterbore, a diameter of the common aperture being larger than a diameter of the distal crimp; and
   advancing the distal crimp through the common aperture.

7. The method of claim 1, wherein the plurality of drive cables comprises first and second drive cables operatively coupled to the first jaw, and third and fourth drive cables operatively coupled to the second jaw, and wherein detaching the plurality of drive cables from the first and second jaws comprises:

dislodging distal crimps attached to distal ends of the first and second drive cables from first and second counterbores, respectively, defined in the first jaw;

dislodging distal crimps attached to distal ends of the third and fourth drive cables from third and fourth counterbores, respectively, defined in the second jaw;

aligning the distal crimps of the first and second drive cables with a first common aperture defined in the first jaw and contiguous with the first and second counterbores, a diameter of the first common aperture being larger than a diameter of the distal crimps of the first and second drive cables;

aligning the distal crimps of the third and fourth drive cables with a second common aperture defined in the second jaw and contiguous with the third and fourth counterbores, a diameter of the second common aperture being larger than a diameter of the distal crimps of the third and fourth cables;

advancing the distal crimps of the first and second drive cables thorough the first common aperture; and advancing the distal crimps of the third and fourth drive cables thorough the second common aperture.

8. The method of claim 1, wherein the surgical tool further includes a proximal clevis sleeve operatively coupled to the wrist and the distal end of the elongate shaft is receivable within the proximal clevis sleeve, and a distal seal assembly arranged within the proximal clevis sleeve and through which the plurality of drive cables extend, and wherein removing the end effector and the wrist from proximal portions of the surgical tool comprises:

detaching the plurality of drive cables from the first and second jaws;

pulling the plurality of drive cables through and out of engagement with the wrist; and moving the end effector and the wrist distally away from the proximal portions of the surgical tool and thereby removing the distal seal assembly from the proximal clevis sleeve.

9. The method of claim 8, wherein a proximal crimp is secured to a proximal end of each drive cable and the surgical tool further includes a plurality of hypotubes arranged within the elongate shaft, each hypotube being configured to receive the proximal crimp of a corresponding one of the drive cables, the method further comprising:

detaching each proximal crimp from the plurality of hypotubes; and replacing at least one of the plurality of drive cables and the distal seal assembly, wherein the consumable comprises the at least one of the plurality of drive cables and the distal seal assembly.

10. The method of claim 1, wherein the plurality of drive cables comprises first and second drive cables operatively coupled to the first jaw, and third and fourth drive cables operatively coupled to the second jaw, each drive cable having a distal crimp secured to a distal end and a proximal crimp secured to a proximal end, and wherein replacing the consumable of the surgical tool comprises replacing one or more of the plurality of drive cables.

11. A method of replacing a consumable of a surgical tool that includes:

a drive housing;

an elongate shaft extending distally from the drive housing;

an end effector arranged at a distal end of the elongate shaft and including opposing first and second jaws;

a wrist interposing the distal end of the elongate shaft and the end effector; and a plurality of drive cables extending proximally from the end effector and through the wrist, wherein the method comprises:

moving the elongate shaft proximally away from the end effector and into an interior of the drive housing;

detaching the plurality of drive cables from the first and second jaws;

displacing the end effector and the wrist distally; and replacing a consumable of the surgical tool.

12. The method of claim 11, wherein the surgical tool further includes a proximal clevis sleeve operatively coupled to the wrist and the distal end of the elongate shaft is received within the proximal clevis sleeve, and wherein moving the elongate shaft proximally comprises:

applying opposing radial loads on opposite sides of the proximal clevis sleeve and thereby elastically deforming the proximal clevis sleeve;

dislodging one or more projections defined on an inner radial surface of the proximal clevis sleeve from one or more corresponding grooves defined on an outer radial surface of the elongate shaft when the proximal clevis sleeve elastically deforms; and moving the elongate shaft proximally once the one or more projections are dislodged from the one or more corresponding grooves.

13. The method of claim 11, wherein the wrist includes a proximal clevis having opposing first and second arms laterally offset from each other and extending distally, each arm defining an open-ended slot that opens distally, and the surgical tool further includes first and second sets of pulleys rotatably mounted to the proximal clevis at first and second axles, respectively, and wherein detaching the plurality of drive cables from the first and second jaws is preceded by:

moving the end effector distally relative to the wrist and thereby moving the first axle distally within the open-ended slots; and separating the first set of pulleys from the second set of pulleys as the first axle moves distally within the open-ended slots.

14. The method of claim 13, wherein each open-ended slot defines a first aperture and a second aperture contiguous with and located distal to the first aperture, and wherein moving the first axle distally within the open-ended slots comprises flexing opposing portions of each arm radially outward as the first axle moves distally within the open-ended slots and transitions from the first aperture to the second aperture.

15. The method of claim 11, wherein a distal crimp is secured to a distal end of each drive cable, and wherein detaching the plurality of drive cables from the first and second jaws comprises:

dislodging the distal crimp from a counterbore defined in a corresponding one of the first and second jaws.

16. The method of claim 11, wherein the plurality of drive cables comprises first and second drive cables operatively coupled to the first jaw, and third and fourth drive cables operatively coupled to the second jaw, and wherein detaching the plurality of drive cables from the first and second jaws comprises:

dislodging distal crimps attached to distal ends of the first and second drive cables from first and second counterbores, respectively, defined in the first jaw;

dislodging distal crimps attached to distal ends of the third and fourth drive cables from third and fourth counterbores, respectively, defined in the second jaw;

aligning the distal crimps of the first and second drive cables with a first common aperture defined in the first jaw and contiguous with the first and second counterbores, a diameter of the first common aperture being larger than a diameter of the distal crimps of the first and second drive cables;

aligning the distal crimps of the third and fourth drive cables with a second common aperture defined in the second jaw and contiguous with the third and fourth counterbores, a diameter of the second common aperture being larger than a diameter of the distal crimps of the third and fourth cables;

advancing the distal crimps of the first and second drive cables thorough the first common aperture; and advancing the distal crimps of the third and fourth drive cables thorough the second common aperture.

17. The method of claim 11, wherein the surgical tool further includes a proximal clevis sleeve operatively coupled to the wrist and the distal end of the elongate shaft is receivable within the proximal clevis sleeve, and a distal seal assembly arranged within the proximal clevis sleeve and through which the plurality of drive cables extend, and wherein removing the end effector and the wrist from proximal portions of the surgical tool comprises:

detaching the plurality of drive cables from the first and second jaws;

pulling the plurality of drive cables through and out of engagement with the wrist; and moving the end effector and the wrist distally away from the proximal portions of the surgical tool and thereby removing the distal seal assembly from the proximal clevis sleeve.

18. The method of claim 17, wherein a proximal crimp is secured to a proximal end of each drive cable and the surgical tool further includes a plurality of hypotubes arranged within the elongate shaft, each hypotube being configured to receive the proximal crimp of a corresponding one of the drive cables, the method further comprising:

detaching each proximal crimp from the plurality of hypotubes; and replacing at least one of the plurality of drive cables and the distal seal assembly, wherein the consumable comprises the at least one of the plurality of drive cables and the distal seal assembly.

19. The method of claim 11, wherein the plurality of drive cables comprises first and second drive cables operatively coupled to the first jaw, and third and fourth drive cables operatively coupled to the second jaw, each drive cable having a distal crimp secured to a distal end and a proximal crimp secured to a proximal end, and wherein replacing the consumable of the surgical tool comprises replacing one or more of the plurality of drive cables.

20. A method, comprising:

moving an elongate shaft of a surgical tool proximally away from an end effector of the surgical tool and into an interior of a drive housing of the surgical tool;

detaching drive cables from the end effector based on moving the elongate shaft proximally;

displacing the end effector and the wrist distally relative to the drive housing based on detaching the drive cables; and replacing a consumable of the surgical tool based on displacing the end effector and wrist distally.

* * * * *